US005891685A

United States Patent [19]

Yamagishi et al.

[11] Patent Number: 5,891,685

[45] Date of Patent: Apr. 6, 1999

[54] METHOD FOR PRODUCING ESTER OF (S)-γ-HALOGENATED-β-HYDROXYBUTYRIC ACID

[75] Inventors: Masahiro Yamagishi, Yokohama; Yukie Takai, Chiyoda-ku; Takashi Mikawa, Yokohama; Mari Hara, Yokohama; Makoto Ueda, Yokohama; Akiko Ohara, Yokohama, all of Japan

[73] Assignee: Mitsubishi Chemical Corporation, Tokyo, Japan

[21] Appl. No.: 867,820

[22] Filed: Jun. 3, 1997

[30] Foreign Application Priority Data

Jun. 3, 1996 [JP] Japan .................................... 8-140087

[51] Int. Cl.[6] ................................ C12P 13/00; C12P 7/62

[52] U.S. Cl. ......................... 435/1.32; 435/132; 435/171; 435/254.1; 435/255.1; 435/280

[58] Field of Search .................................... 435/135, 280, 435/254.1, 255.1, 132, 171, 128, 254.11

[56] References Cited

U.S. PATENT DOCUMENTS

| | | | |
|---|---|---|---|
| 4,642,290 | 2/1987 | Sih | 435/128 |
| 4,710,468 | 12/1987 | Sih | 435/135 |
| 4,933,282 | 6/1990 | Hasegawa et al. | 435/135 |
| 5,413,921 | 5/1995 | Onishi et al. | 435/135 |
| 5,559,030 | 9/1996 | Matsuyama et al. | 435/820 |
| 5,700,670 | 12/1997 | Yamagishi et al. | 435/128 |

OTHER PUBLICATIONS

Japanese Laid–Open Patent Publication No. 63–309195 (1988).

Japanese Laid–Open Patent Publication No. 61–146191 (1986) (corresponding to Japanese patent Publication No. 4–7195 (1992)).

*Primary Examiner*—Keith D. Hendricks
*Assistant Examiner*—Bradley S. Mayhew
*Attorney, Agent, or Firm*—Wenderoth, Lind & Ponack, L.L.P.

[57] ABSTRACT

Microbial cells and/or a preparation thereof of a microorganism is allowed to act on ester of γ-halogenated-acetoacetic acid, and its carbonyl group at β-position is stereospecifically reduced to produce ester of (S)-γ-halogenated-β-hydroxybutyric acid in a short period of time at a highly accumulated degree and at a high yield, the microorganism being selected from the group consisting of those belonging to the genera Phoma, Nectria, Pseudonectria, Spondylocladium, Melanospora, Metarhizium, Gliocladium, Pestalotia, Pestalotiopsis, Curvularia, Hormonema, Sydowia, Sarcinomyces, Dothiora, Xanthothecium, Dothidea, Pringsheimia, and Selenophoma.

23 Claims, 10 Drawing Sheets

```
Candida albicans(X53497)            1117:AAACTTAAAGGAATTGACGGAAGGGCACC AC CAGGAGTGGAGCCTGCGGCTTAATTTG 1174 (SEQ ID NO: 1 )
A.pul.var.pullulans ATCC34621       1117:............................. ..-........................... 1174 (SEQ ID NO: 2 )
A.pul.var.pullulans CBS123.37       1117:.............................-.. ....C...................... 1174 (SEQ ID NO: 3 )
A.pul.var.pullulans CBS146.30       1117:.............................-..-....C...................... 1174 (SEQ ID NO: 4 )
A.pul.var.pullulans CBS701.76       1117:.............................-.. ....C...T.................. 1174 (SEQ ID NO: 5 )
A.pul.var.pullulans MCI3251         1117:.............................-..-....C...................... 1174 (SEQ ID NO: 6 )
A.pul.var.pullulans MCI3252         1117:........................-....A..-....C......-............... 1173 (SEQ ID NO: 7 )
A.microsticutum IFO32070            1117:..........A................-.-..-....C....-................. 1172 (SEQ ID NO: 8 )
Dothiora cannavinae CBS737.71       1117:.............................-.. ....C...................... 1174 (SEQ ID NO: 9 )
Dothiora elliptica CBS736.71        1117:.............................-..-....C...................... 1174 (SEQ ID NO:10)
Dothiora phaeosperma CBS870.71      1117:..........A..................-..-....C...................... 1174 (SEQ ID NO:11)
Dothiora rhamni alpinae CBS745.71   1117:..........A..................-..-....C...................... 1174 (SEQ ID NO:12)
Hormonema sp.MCI3287                1117:..........A.................. ..A...C...... ............... 1174 (SEQ ID NO:13)
Hormonema sp.MCI3468                1117:..........A..................-..-....C...................... 1174 (SEQ ID NO:14)
Dothiora europaea CBS738.71         1117:..........................T..-..-....C.........A............ 1174 (SEQ ID NO:15)
Dothiora laureolae CBS744.71        1117:..........A..................-..-....C...................... 1174 (SEQ ID NO:16)
Dothiora schizospora CBS189.55      1117:..........A..................-..-....C...................... 1174 (SEQ ID NO:17)
Hormonema prunorum CBS933.72        1117:.............................-..-....C...................... 1174 (SEQ ID NO:18)
Sydowia polyspora CBS116.29         1117:..............A..............-..-....C...................... 1174 (SEQ ID NO:19)
Pringsheimia sepincola CBS748.71    1117:..........A..................-..-....C...................... 1174 (SEQ ID NO:20)
Selenophoma mahoniae CBS388.92      1117:..........A..................-..-....C...................... 1174 (SEQ ID NO:21)
Discosphaerian fagi CBS171.93       1117:..........A..................-..-....C...................... 1174 (SEQ ID NO:22)
Dothidea noxia CBS171.34            1117:..........A..................-..-A..G...................... 1174 (SEQ ID NO:23)
Dothidea muelleri CBS191.58         1117:..........A..................-..-....C...................... 1174 (SEQ ID NO:24)
Dothidea sambuci CBS197.58          1117:..........A..................-..-....C...................... 1174 (SEQ ID NO:25)
Selenophoma donacis CBS417.51       1117:..........A..................-..-....G...................... 1174 (SEQ ID NO:26)
Dothiora moravica CBS266.59         1117:..........A..................-..-....C...................... 1174 (SEQ ID NO:27)
Pringsheimia karelii CBS374.59      1117:..........A..................-..-....C...................... 1174 (SEQ ID NO:28)
Dothidea berberidis CBS186.58       1117:..........A..................-..-....C...................... 1174 (SEQ ID NO:29)
Sydowia agharkari CBS434.61         1117:..........A..................-..-....C...................... 1174 (SEQ ID NO:30)
Selenophoma linicola CBS468.48      1117:..........A..................-..-....C...................... 1174 (SEQ ID NO:31)
                                         ********** *** *********  * * **  *** ****  * ** ***********
```

FIG. 1

```
Candida albicans(X53497)             1175:ACTCAACACGGGGAAACTCACCAGGTCCAGACACAATAA-GGATTGACAGATTGAGAGCT 1233(SEQ ID NO: 1 )
A.pul.var.pullulans ATCC34621        1175:.......................................-.................... 1233(SEQ ID NO: 2 )
A.pul.var.pullulans CBS123.37        1175:.......................................-.................... 1233(SEQ ID NO: 3 )
A.pul.var.pullulans CBS146.30        1175:.......................................-.................... 1233(SEQ ID NO: 4 )
A.pul.var.pullulans CBS701.76        1175:...................................T...-.................... 1233(SEQ ID NO: 5 )
A.pul.var.pullulans MCI3251          1175:.......................................-.................... 1233(SEQ ID NO: 6 )
A.pul.var.pullulans MCI3252          1174:.......................................-.................... 1232(SEQ ID NO: 7 )
A.microsticutum IFO32070             1173:.......................................G.................... 1232(SEQ ID NO: 8 )
Dothiora cannavinae CBS737.71        1175:.......................................-.................... 1233(SEQ ID NO: 9 )
Dothiora elliptica CBS736.71         1175:.......................................-.................... 1233(SEQ ID NO:10)
Dothiora phaeosperma CBS870.71       1175:.......................................-.................... 1233(SEQ ID NO:11)
Dothiora rhamni-alpinae CBS745.71    1175:.......................................-.................... 1233(SEQ ID NO:12)
Hormonema sp.MCI3287                 1175:.......................................-.................... 1233(SEQ ID NO:13)
Hormonema sp.MCI3468                 1175:.......................................-.................... 1233(SEQ ID NO:14)
Dothiora europaea CBS738.71          1175:......................................-C.................... 1233(SEQ ID NO:15)
Dothiora laureolae CBS744.71         1175:.......................................-.................... 1233(SEQ ID NO:16)
Dothiora schizospora CBS189.55       1175:.......................................-.................... 1233(SEQ ID NO:17)
Hormonema prunorum CBS933.72         1175:.......................................-.................... 1233(SEQ ID NO:18)
Sydowia polyspora CBS116.29          1175:.......................................-.................... 1233(SEQ ID NO:19)
Pringsheimia sepincola CBS748.71     1175:.......................................-.................... 1233(SEQ ID NO:20)
Selenophoma mahoniae CBS388.92       1175:.......................................-.................... 1233(SEQ ID NO:21)
Discosphaerian fagi CBS171.93        1175:.......................................-.................... 1233(SEQ ID NO:22)
Dothidea noxia CBS171.34             1175:....................................CT.-.................... 1233(SEQ ID NO:23)
Dothidea muelleri CBS191.58          1175:.......................................-.................... 1233(SEQ ID NO:24)
Dothidea sambuci CBS197.58           1175:.......................................-.................... 1233(SEQ ID NO:25)
Selenophoma donacis CBS417.51        1175:.....................................G.-.................... 1233(SEQ ID NO:26)
Dothiora moravica CBS266.59          1175:................................TGA....-.................... 1233(SEQ ID NO:27)
Pringsheimia karelii CBS374.59       1175:.......................................-............G....... 1233(SEQ ID NO:28)
Dothidea berberidis CBS186.58        1175:.......................................-.................... 1233(SEQ ID NO:29)
Sydowia agharkari CBS434.61          1175:.......................................-.................... 1233(SEQ ID NO:30)
Selenophoma linicola CBS468.48       1175:.......................................-.................... 1233(SEQ ID NO:31)
                                          *******************************   *    ************ *******
```

F I G. 2

```
Candida albicans(X53497)          1234:CTTTCTTGATTTTGTGGGTGGTGGTGCATGGCCGTTCTTAGTTGGTGGAGTGATTTGTCT 1293(SEQ ID NO: 1 )
A.pul.var.pullulans ATCC34621     1234:............C............................................... 1293(SEQ ID NO: 2 )
A.pul.var.pullulans CBS123.37     1234:........................................................A... 1293(SEQ ID NO: 3 )
A.pul.var.pullulans CBS146.30     1234:............................................................ 1293(SEQ ID NO: 4 )
A.pul.var.pullulans CBS701.76     1234:............C.....................C......................... 1293(SEQ ID NO: 5 )
A.pul.var.pullulans MCI3251       1234:............................................................ 1293(SEQ ID NO: 6 )
A.pul.var.pullulans MCI3252       1233:............................................................ 1292(SEQ ID NO: 7 )
A.microsticutum IFO32070          1233:............................................................ 1292(SEQ ID NO: 8 )
Dothiora cannavinac CBS737.71     1234:............................................................ 1293(SEQ ID NO: 9 )
Dothiora elliptica CBS736.71      1234:............................................................ 1293(SEQ ID NO:10)
Dothiora phaeosperma CBS870.71    1234:............................................................ 1293(SEQ ID NO:11)
Dothiora rhamni-alpinae CBS745.71 1234:............................................................ 1293(SEQ ID NO:12)
Hormonema sp.MCI3287              1234:............................................................ 1293(SEQ ID NO:13)
Hormonema sp.MCI3468              1234:............................................................ 1293(SEQ ID NO:14)
Dothiora europaea CBS738.71       1234:..C..............C...C.......................C.............. 1293(SEQ ID NO:15)
Dothiora laureolae CBS744.71      1234:............................................................ 1293(SEQ ID NO:16)
Dothiora schizospora CBS189.55    1234:........................................A................... 1293(SEQ ID NO:17)
Hormonema prunorum CBS933.72      1234:............CA................C............................. 1293(SEQ ID NO:18)
Sydowia polyspora CBS116.29       1234:............C.....................C......................... 1293(SEQ ID NO:19)
Pringsheimia sepincola CBS748.71  1234:............................................................ 1293(SEQ ID NO:20)
Selenophoma mahoniae CBS388.92    1234:............................................................ 1293(SEQ ID NO:21)
Discosphaerian fagi CBS171.93     1234:............................................................ 1293(SEQ ID NO:22)
Dothidea noxia CBS171.34          1234:............................................................ 1293(SEQ ID NO:23)
Dothidea muelleri CBS191.58       1234:........................................C................... 1293(SEQ ID NO:24)
Dothidea sambuci CBS197.58        1234:............................................................ 1293(SEQ ID NO:25)
Selenophoma donacis CBS417.51     1234:............................................................ 1293(SEQ ID NO:26)
Dothiora moravica CBS266.59       1234:............TCA............................................. 1293(SEQ ID NO:27)
Pringsheimia karelii CBS374.59    1234:............................................................ 1293(SEQ ID NO:28)
Dothidea berberidis CBS186.58     1234:............................................................ 1293(SEQ ID NO:29)
Sydowia agharkari CBS434.61       1234:............................................................ 1293(SEQ ID NO:30)
Selenophoma linicola CBS468.48    1234:............................................................ 1293(SEQ ID NO:31)
                                       ** *********    * *** ******** *** ***** **** ********** ***
```

FIG. 3

```
Candida albicans(X53497)          1294:GCTTAATTGCGATAACGAACGAGACCTTAACCTACTAAATAGTGCTGCTAGCATTTGCTG 1353(SEQ ID NO: 1 )
A.pul.var.pullulans ATCC34621     1294:.................................G.......CC.G..CC..-....GC. 1352(SEQ ID NO: 2 )
A.pul.var.pullulans CBS123.37     1294:.................................G.......CC.G..CC..-....GC. 1352(SEQ ID NO: 3 )
A.pul.var.pullulans CBS146.30     1294:.................................G.......CC.G..CC..-....GC. 1352(SEQ ID NO: 4 )
A.pul.var.pullulans CBS701.76     1294:.................................G.......CC.G..CC..-....GC. 1352(SEQ ID NO: 5 )
A.pul.var.pullulans MCI3251       1294:.................................G.......CC.G..CC..-....GC. 1352(SEQ ID NO: 6 )
A.pul.var.pullulans MCI3252       1293:.................................G.......CC.G..CC..-....GC. 1351(SEQ ID NO: 7 )
A.microsticutum IFO32070          1293:...........................-.....G.......CC.G..CC..-....GC. 1350(SEQ ID NO: 8 )
Dothiora cannavinae CBS737.71     1294:.................................G.......CC.G..CC..-....GC. 1352(SEQ ID NO: 9 )
Dothiora elliptica CBS736.71      1294:.................................G.......CC.G..CC..-....GC. 1352(SEQ ID NO:10)
Dothiora phaeosperma CBS870.71    1294:...................G....-........G.......CC.G..CC..-....GC. 1351(SEQ ID NO:11)
Dothiora rhamni-alpinae CBS745.71 1294:.................................G.......CC.G..CC..-....GC. 1352(SEQ ID NO:12)
Hormonema sp.MCI3287              1294:.................................G.......CC.G..CC..-....GC. 1352(SEQ ID NO:13)
Hormonema sp.MCI3468              1294:.................................G.......CC.G..CC..-....GC. 1352(SEQ ID NO:14)
Dothiora europaea CBS738.71       1294:.................................G.......CC.G..CC..-....GC. 1352(SEQ ID NO:15)
Dothiora laureolae CBS744.71      1294:.................................G.......CC.G..CC..-....GC. 1352(SEQ ID NO:16)
Dothiora schizospora CBS189.55    1294:......................A..........G.......CC.G..CC..-....GC. 1352(SEQ ID NO:17)
Hormonema prunorum CBS933.72      1294:.................................G.......CC.G..CC..-....GC. 1352(SEQ ID NO:18)
Sydowia polyspora CBS116.29       1294:.................................G.......CC.G.TCC..-....GC. 1352(SEQ ID NO:19)
Pringsheimia sepincola CBS748.71  1294:.................................G.......CC.G..CC..-....GC. 1352(SEQ ID NO:20)
Selenophoma mahoniae CBS388.92    1294:.................................G.......CC.G..CC..-....GC. 1352(SEQ ID NO:21)
Discosphaerian fagi CBS171.93     1294:.................................G.......CC.G..CC..-....GC. 1352(SEQ ID NO:22)
Dothidea noxia CBS171.34          1294:.................................G.......CC.GTTCC..-..A.GC. 1352(SEQ ID NO:23)
Dothidea muelleri CBS191.58       1294:.........................-.......G.......CC.G..CC..-....GC. 1351(SEQ ID NO:24)
Dothidea sambuci CBS197.58        1294:.................................G.......CC.G..CC..-....GC. 1352(SEQ ID NO:25)
Selenophoma donacis CBS417.51     1294:.................................G.......CC.GTA.T..-....GCA 1352(SEQ ID NO:26)
Dothiora moravica CBS266.59       1294:.................................G.......CCAG......-....GCT 1352(SEQ ID NO:27)
Pringsheimia karelii CBS374.59    1294:.................................G.......CC.G..CC..-....GC. 1352(SEQ ID NO:28)
Dothidea berberidis CBS186.58     1294:.................................G.......CC.G..CC..-....GC. 1352(SEQ ID NO:29)
Sydowia agharkari CBS434.61       1294:.................................G.......CC.G..CC..-....GC. 1352(SEQ ID NO:30)
Selenophoma linicola CBS468.48    1294:.................................G.......CC.G..CC..-....GC. 1352(SEQ ID NO:31)
                                       ****************** ** ** * ***** ********       ** ** *
```

FIG. 4

```
Candida albicans(X53497)              1354:GTATAGTCACTTCTTAGAGGGACTATCGACTCCAAGT CGATGGAAGTTTGAGGCAATAA 1412(SEQ ID NO: 1 )
A.pul.var.pullulans ATCC34621         1353:.GTCGCCGG...................G..-....C-...................... 1410(SEQ ID NO: 2 )
A.pul.var.pullulans CBS123.37         1353:.GTCGCCGG...................G..-....C-...................... 1410(SEQ ID NO: 3 )
A.pul.var.pullulans CBS146.30         1353:.GTCGCCGG...................G..-....C-...................... 1410(SEQ ID NO: 4 )
A.pul.var.pullulans CBS701.76         1353:.GTCGTCGG...................G..-....CG...................... 1411(SEQ ID NO: 5 )
A.pul.var.pullulans MCI3251           1353:.GTCGCCGG...................G.. ....C-...................... 1410(SEQ ID NO: 6 )
A.pul.var.pullulans MCI3252           1352:.GTCGCCGG...................G..-....C-...................... 1409(SEQ ID NO: 7 )
A.microsticutum IFO32070              1351:.GTCGCCGG...................G..-....C-...................... 1408(SEQ ID NO: 8 )
Dothiora cannavinae CBS737.71         1353:.GTCGCCGG...................G..-....C-...................... 1410(SEQ ID NO: 9 )
Dothiora elliptica CBS736.71          1353:.GTCGCCGG...................G..-....C-...................... 1410(SEQ ID NO:10)
Dothiora phaeosperma CBS870.71        1352:.GTCGCCGG...................G..-....C-...................... 1409(SEQ ID NO:11)
Dothiora rhamni-alpinae CBS745.71     1353:.GTCGCCGG...................G..-....C-...................... 1410(SEQ ID NO:12)
Hormonema sp.MCI3287                  1353:.GTCGCCGG...................G..-....C-...................... 1410(SEQ ID NO:13)
Hormonema sp.MCI3468                  1353:.GTCGCCGG...................G..-....C-...................... 1410(SEQ ID NO:14)
Dothiora europaea CBS738.71           1353:.GTCGCCGG...................G..-....C-...................... 1410(SEQ ID NO:15)
Dothiora laureolae CBS744.71          1353:.GTCGCCGG...................G..-....C-...................... 1410(SEQ ID NO:16)
Dothiora schizospora CBS189.55        1353:.GTCGCCGG...................G..-....C-...................... 1410(SEQ ID NO:17)
Hormonema prunorum CBS933.72          1353:.GTCGCCGG...................G..-....C-...................... 1410(SEQ ID NO:18)
Sydowia polyspora CBS116.29           1353:.GCCGCCGG...................G..-....C-...................... 1410(SEQ ID NO:19)
Pringsheimia sepincola CBS748.71      1353:.GTCGCCGG...................G..-....C-...................... 1410(SEQ ID NO:20)
Selenophoma mahoniae CBS388.92        1353:.GTCGCCGG...................G..-....C-...................... 1410(SEQ ID NO:21)
Discosphaerian fagi CBS171.93         1353:.GTCGCCGG...................G..-....C-...................... 1410(SEQ ID NO:22)
Dothidea noxia CBS171.34              1353:.A.CGC.GG...................G..-....C-...................... 1410(SEQ ID NO:23)
Dothidea muelleri CBS191.58           1352:.GTCGCCGG...................G..-....C-...................... 1409(SEQ ID NO:24)
Dothidea sambuci CBS197.58            1353:.GTCGCCGG...................G..-....C-...................... 1410(SEQ ID NO:25)
Selenophoma donacis CBS417.51         1353:...CGCCGG...................G..-....C-...................... 1410(SEQ ID NO:26)
Dothiora moravica CBS266.59           1353:.GTCGCCGG...................G..-....C-...................... 1410(SEQ ID NO:27)
Pringsheimia karelii CBS374.59        1353:.GTCGCCGG...................G..-....C-...................... 1410(SEQ ID NO:28)
Dothidea berberidis CBS186.58         1353:.GTCGCCGG...................G..-....C-...................... 1410(SEQ ID NO:29)
Sydowia agharkari CBS434.61           1353:.GTCGCCGG.........A.........G..-....C-...................... 1410(SEQ ID NO:30)
Selenophoma linicola CBS468.48        1353:.GTCGCCGG...................G..-....C-...................... 1410(SEQ ID NO:31)
                                           *        ********* ********* ** ****  *********************
```

FIG. 5

```
Candida albicans(X53497)                1413:CAGGTCTGTGATGCCCTTAGACGTTCTGGGCCGCACGCGCGCTACACTGACGGAGCCAGC 1472(SEQ ID NO: 1 )
A.pul.var.pullulans ATCC34621           1411:....................T..............................A......A. 1470(SEQ ID NO: 2 )
A.pul.var.pullulans CBS123.37           1411:....................T..............................A......A. 1470(SEQ ID NO: 3 )
A.pul.var.pullulans CBS146.30           1411:....................T..............................A......A. 1470(SEQ ID NO: 4 )
A.pul.var.pullulans CBS701.76           1412:....................T..............................A......A. 1471(SEQ ID NO: 5 )
A.pul.var.pullulans MCI3251             1411:....................T..............................A......A. 1470(SEQ ID NO: 6 )
A.pul.var.pullulans MCI3252             1410:....................T..............................A......A. 1469(SEQ ID NO: 7 )
A.microsticutum IFO32070                1409:....................T..............................A......A. 1468(SEQ ID NO: 8 )
Dothiora cannavinae CBS737.71           1411:....................T..............................A......A. 1470(SEQ ID NO: 9 )
Dothiora elliptica CBS736.71            1411:....................T..............................A......A. 1470(SEQ ID NO:10)
Dothiora phaeosperma CBS870.71          1410:....................T..............................A......A. 1469(SEQ ID NO:11)
Dothiora rhamni-alpinae CBS745.71       1411:....................T..............................A......A. 1470(SEQ ID NO:12)
Hormonema sp.MCI3287                    1411:....................T..............................A......A. 1470(SEQ ID NO:13)
Hormonema sp.MCI3468                    1411:....................T..............................A......A. 1470(SEQ ID NO:14)
Dothiora europaea CBS738.71             1411:....................T..............................A......A. 1470(SEQ ID NO:15)
Dothiora laureolae CBS744.71            1411:....................T..............................A......A. 1470(SEQ ID NO:16)
Dothiora schizospora CBS189.55          1411:....................T..............................A......A. 1470(SEQ ID NO:17)
Hormonema prunorum CBS933.72            1411:....................T..............................A......A. 1470(SEQ ID NO:18)
Sydowia polyspora CBS116.29             1411:....................T..............................A......A. 1470(SEQ ID NO:19)
Pringsheimia sepincola CBS748.71        1411:....................T..............................A......A. 1470(SEQ ID NO:20)
Selenophoma mahoniae CBS388.92          1411:....................T..............................A......A. 1470(SEQ ID NO:21)
Discosphaerian fagi CBS171.93           1411:....................T..............................A......A. 1470(SEQ ID NO:22)
Dothidea noxia CBS171.34                1411:....................T..............................A........ 1470(SEQ ID NO:23)
Dothidea muelleri CBS191.58             1410:....................T..............................A......A. 1469(SEQ ID NO:24)
Dothidea sambuci CBS197.58              1411:....................T..............................A......A. 1470(SEQ ID NO:25)
Selenophoma donacis CBS417.51           1411:....................T....................T.................. 1470(SEQ ID NO:26)
Dothiora moravica CBS266.59             1411:....................T..............................A......A. 1470(SEQ ID NO:27)
Pringsheimia karelii CBS374.59          1411:....................T..............................A......A. 1470(SEQ ID NO:28)
Dothidea berberidis CBS186.58           1411:....................T..............................A......A. 1470(SEQ ID NO:29)
Sydowia agharkari CBS434.61             1411:....................T..............................A......A. 1470(SEQ ID NO:30)
Selenophoma linicola CBS468.48          1411:....................T..............................A......A. 1470(SEQ ID NO:31)
                                             ******************** ******************** ********* ****** *
```

FIG. 6

```
Candida albicans(X53497)           1473:GAGTA TAAGCCTTGGCCG AGAGGTCTGGGAAATCTTGTGAAACTCCGTCGTGCTGGGG 1530(SEQ ID NO:1)
A.pul.var.pullulans ATCC34621      1471:....TCATTT.....C...G.AG...-....T.....C..T......T........... 1529(SEQ ID NO:2)
A.pul.var.pullulans CBS123.37      1471:....TCATTT.....C...G.AG...-....T........T......T........... 1529(SEQ ID NO:3)
A.pul.var.pullulans CBS146.30      1471:....TCATTT.....C...G.AG...-....T........T......T........... 1529(SEQ ID NO:4)
A.pul.var.pullulans CBS701.76      1472:....TCATTT.....C...G.AG...-....T........T......T........... 1530(SEQ ID NO:5)
A.pul.var.pullulans MCI3251        1471:....TCATTT.....C...G.AG...-....T........T......T........... 1529(SEQ ID NO:6)
A.pul.var.pullulans MCI3252        1470:....TCATTT.....C...G.AG...-....T........T......T........... 1528(SEQ ID NO:7)
A.microsticutum IFO32070           1469:....TCATTT.....C...G.AG...-....T........T......T........... 1527(SEQ ID NO:8)
Dothiora cannavinae CBS737.71      1471:....TCATCA.........G.A-........T........T......T........... 1529(SEQ ID NO:9)
Dothiora elliptica CBS736.71       1471:....TCATCA.........G.A ........T........T......T........... 1529(SEQ ID NO:10)
Dothiora phaeosperma CBS870.71     1470:....TCATCA.........G.A-........T........T......T........... 1528(SEQ ID NO:11)
Dothiora rhamni-alpinae CBS745.71  1471:....TCATCA.........G.A-........T........T......T........... 1529(SEQ ID NO:12)
Hormonema sp.MCI3287               1471:....TCATCA.........G.A-........T........T......T........... 1529(SEQ ID NO:13)
Hormonema sp.MCI3468               1471:....TCATCA.........G.A-........T........T......T........... 1529(SEQ ID NO:14)
Dothiora europaea CBS738.71        1471:...ATCATCA.....-...G.A-........T........T......T........... 1528(SEQ ID NO:15)
Dothiora laureolae CBS744.71       1471:....TCATCA.........G.A--.......T........T......T........... 1528(SEQ ID NO:16)
Dothiora schizospora CBS189.55     1471:....TCATCA.........G.A--.......T........T......T........... 1528(SEQ ID NO:17)
Hormonema prunorum CBS933.72       1471:....TCATCA.....A...G.A-........T........T......T........... 1529(SEQ ID NO:18)
Sydowia polyspora CBS116.29        1471:....TCATCA.....T...G.AG.A.-....T........T......T........... 1529(SEQ ID NO:19)
Pringsheimia sepincola CBS748.71   1471:....TCATTT.....T...-.A.........T........T......T........... 1529(SEQ ID NO:20)
Selenophoma mahoniae CBS388.92     1471:....TCATTT.....C...G.AG...-....T........T......T........... 1529(SEQ ID NO:21)
Discosphaerian fagi CBS171.93      1471:....TCATTT.....C...G.AG...-....T........T......T........... 1529(SEQ ID NO:22)
Dothidea noxia CBS171.34           1471:....TC--CT.......T.G.A.-.C.C...T...............T........... 1527(SEQ ID NO:23)
Dothidea muelleri CBS191.58        1470:....TCATCA.........-.A.........T........T......T........... 1528(SEQ ID NO:24)
Dothidea sambuci CBS197.58         1471:....TCATCA.........-.A.........T........T......T........... 1529(SEQ ID NO:25)
Selenophoma donacis CBS417.51      1471:...-TAC-TC.........G.A-..C.C...T........T...................... 1527(SEQ ID NO:26)
Dothiora moravica CBS266.59        1471:....TC.TCA.........-.A.........T........T......T........... 1529(SEQ ID NO:27)
Pringsheimia karelii CBS374.59     1471:....TCATTT.........-.A.........T........T......T........... 1529(SEQ ID NO:28)
Dothidea berberidis CBS186.58      1471:....TCATCA.........G.A-........T........T......T........... 1529(SEQ ID NO:29)
Sydowia agharkari CBS434.61        1471:....TCATTT.........-.A.........T........T......T........... 1529(SEQ ID NO:30)
Selenophoma linicola CBS468.48     1471:....TCATTT.........G.A-........T........T......T........... 1529(SEQ ID NO:31)
                                           ***      ***** * * *      *** ***** ** ****** ************
```

FIG. 7

```
Candida albicans(X53497)               1531:ATAGAGCATTGTAATTGTTGCTCTTCAACGAGG AATTCCTAGTAAGCGCAAGTCATCAG 1589(SEQ ID NO: 1 )
A.pul.var.pullulans ATCC34621          1530:...........C...A.................-...G..........T.C......... 1588(SEQ ID NO: 2 )
A.pul.var.pullulans CBS123.37          1530:...........C...A.................-...G..........T.C......... 1588(SEQ ID NO: 3 )
A.pul.var.pullulans CBS146.30          1530:...........C...A.................-...G..........T.C......... 1588(SEQ ID NO: 4 )
A.pul.var.pullulans CBS701.76          1531:...........C...A.................-...G..........T.C......... 1589(SEQ ID NO: 5 )
A.pul.var.pullulans MCI3251            1530:...........C...A.................-...G..........T.C......... 1588(SEQ ID NO: 6 )
A.pul.var.pullulans MCI3252            1529:...........C...A.................-...G..........T.C......... 1587(SEQ ID NO: 7 )
A.microsticutum IFO32070               1528:...........C...A................A-...G..........T.C......... 1586(SEQ ID NO: 8 )
Dothiora cannavinae CBS737.71          1529:...........C...A.................-...G............T......... 1588(SEQ ID NO: 9 )
Dothiora elliptica CBS736.71           1529:...........C...A.................-...G............T......... 1588(SEQ ID NO:10)
Dothiora phaeosperma CBS870.71         1527:...........C...A.................-...G............T......... 1587(SEQ ID NO:11)
Dothiora rhamni-alpinae CBS745.71      1528:...........C...A.................-...G............T......... 1588(SEQ ID NO:12)
Hormonema sp.MCI3287                   1530:...........C...A.................-...G............T......... 1588(SEQ ID NO:13)
Hormonema sp.MCI3468                   1530:...........C...A.................-...G............T......... 1588(SEQ ID NO:14)
Dothiora europaea CBS738.71            1529:...........C...A.................-...G............T......... 1587(SEQ ID NO:15)
Dothiora laureolae CBS744.71           1529:...........C...A.................-...G............T......... 1587(SEQ ID NO:16)
Dothiora schizospora CBS189.55         1529:...........C...A................A-...G............T......... 1587(SEQ ID NO:17)
Hormonema prunorum CBS933.72           1530:...........C...A.................-...G............T........A 1588(SEQ ID NO:18)
Sydowia polyspora CBS116.29            1530:...........C...A.................-...G............T......... 1588(SEQ ID NO:19)
Pringsheimia sepincola CBS748.71       1530:...........C...A..-..............-...G..........T.C......... 1587(SEQ ID NO:20)
Selenophoma mahoniae CBS388.92         1530:...........C...A.................-...G..........T.C......... 1588(SEQ ID NO:21)
Discosphaerian fagi CBS171.93          1530:...........C...A.................-...G..........T.C......... 1588(SEQ ID NO:22)
Dothidea noxia CBS171.34               1528:...........C...A.................-...C...................... 1586(SEQ ID NO:23)
Dothidea muelleri CBS191.58            1529:...........C...A.................-...G............T......... 1587(SEQ ID NO:24)
Dothidea sambuci CBS197.58             1530:...........C...A.................-...G............T......... 1588(SEQ ID NO:25)
Selenophoma donacis CBS417.51          1528:...........C...A.................A...C...................... 1587(SEQ ID NO:26)
Dothiora moravica CBS266.59            1530:...........C...A.................-...G...........GT......... 1588(SEQ ID NO:27)
Pringsheimia karelii CBS374.59         1530:...........C...A.................-...G..........T.C......... 1588(SEQ ID NO:28)
Dothidea berberidis CBS186.58          1530:...........C...A.................-...G............T......... 1588(SEQ ID NO:29)
Sydowia agharkari CBS434.61            1530:...........C...A................A-...G..........T.C......... 1588(SEQ ID NO:30)
Selenophoma linicola CBS468.48         1530:...........C...A.................-...G..........T.C......... 1588(SEQ ID NO:31)
                                            *********** **** *** ********** * *** ***********   *******
```

FIG. 8

```
Candida albicans(X53497)            1590:CTTGCGTTGATTACGT CCCTGCCCTTTGTACACACCGCCCGT 1631(SEQ ID NO: 1 )
A.pul.var.pullulans ATCC34621       1589:.G..............-.......................... 1630(SEQ ID NO: 2 )
A.pul.var.pullulans CBS123.37       1589:.G..............-.......................... 1630(SEQ ID NO: 3 )
A.pul.var.pullulans CBS146.30       1589:.G..............-.......................... 1630(SEQ ID NO: 4 )
A.pul.var.pullulans CBS701.76       1590:.G.............. .......................... 1631(SEQ ID NO: 5 )
A.pul.var.pullulans MCI3251         1589:.G.............. .......................... 1630(SEQ ID NO: 6 )
A.pul.var.pullulans MCI3252         1588:.G..............-.......................... 1629(SEQ ID NO: 7 )
A.microsticutum IFO32070            1587:.G..............-.......................... 1628(SEQ ID NO: 8 )
Dothiora cannavinae CBS737.71       1589:.A..............G.......................... 1631(SEQ ID NO: 9 )
Dothiora elliptica CBS736.71        1589:.A..............-.......................... 1630(SEQ ID NO:10)
Dothiora phaeosperma CBS870.71      1588:.A.............. .......................... 1629(SEQ ID NO:11)
Dothiora rhamni-alpinae CBS745.71   1589:.A..............-.......................... 1630(SEQ ID NO:12)
Hormonema sp.MCI3287                1589:.A.............. .......................... 1630(SEQ ID NO:13)
Hormonema sp.MCI3468                1589:.A..............-.......................... 1630(SEQ ID NO:14)
Dothiora europaea CBS738.71         1588:.A..............G.......................... 1630(SEQ ID NO:15)
Dothiora laureolae CBS744.71        1588:.A..............-.......................... 1629(SEQ ID NO:16)
Dothiora schizospora CBS189.55      1588:.A..............-.......................... 1629(SEQ ID NO:17)
Hormonema prunorum CBS933.72        1589:.A..............-.......................... 1630(SEQ ID NO:18)
Sydowia polyspora CBS116.29         1589:.A..............-.......................... 1630(SEQ ID NO:19)
Pringsheimia sepincola CBS748.71    1588:.G..............-.......................... 1629(SEQ ID NO:20)
Selenophoma mahoniae CBS388.92      1589:.G..............-.......................... 1630(SEQ ID NO:21)
Discosphaerian fagi CBS171.93       1589:.G..............-.......................... 1630(SEQ ID NO:22)
Dothidea noxia CBS171.34            1587:................-.......................... 1628(SEQ ID NO:23)
Dothidea muelleri CBS191.58         1588:.A..............-.......................... 1629(SEQ ID NO:24)
Dothidea sambuci CBS197.58          1589:.A..............-.......................... 1630(SEQ ID NO:25)
Selenophoma donacis CBS417.51       1588:................-.......................... 1629(SEQ ID NO:26)
Dothiora moravica CBS266.59         1589:.A..............-.......................... 1630(SEQ ID NO:27)
Pringsheimia karelii CBS374.59      1589:.G..............-.......................... 1630(SEQ ID NO:28)
Dothidea berberidis CBS186.58       1589:.A..............-.......................... 1630(SEQ ID NO:29)
Sydowia agharkari CBS434.61         1589:.G..............-.......................... 1630(SEQ ID NO:30)
Selenophoma linicola CBS468.48      1589:.G..............-.......................... 1630(SEQ ID NO:31)
                                         * ************** **************************
```

FIG. 9

METHOD FOR PRODUCING ESTER OF (S)-γ-HALOGENATED-β-HYDROXYBUTYRIC ACID

BACKGROUND OF THE INVENTION

1. Field of the Invention

The present invention relates to a method for producing ester of (S)-γ-halogenated-β-hydroxybutyric acid. In particular, the present invention relates to an efficient method for producing ester of (S)-γ-halogenated-β-hydroxybutyric acid having a high optical purity, based on the use of a microorganism belonging to a specified genus or a taxonomic unit.

2. Description of the Related Art

Optically active ester of γ-halogenated-β-hydroxybutyric acid is useful as a raw material for synthesizing optically active compounds or synthetic intermediates thereof, to be utilized for various pharmaceuticals and agricultural chemicals. For example, the optically active ester of γ-halogenated-β-hydroxybutyric acid can be converted into side chain moieties of optically active hydroxy acid derivatives which are common to various HMG-CoA reductase inhibitors (therapeutic agents for hyperlipemia) such as compactin and pravastatin. In order to produce the optically active ester of γ-halogenated-β-hydroxybutyric acid, investigations have been hitherto made to utilize microbial abilities to effect asymmetric reduction. There have been a large number of reports on the production of optically active ester of γ-halogenated-β-hydroxybutyric acid based on such a microbial process.

These, for example, methods include: (1) a method based on the use of microbial cells of a yeast belonging to, for example, the genus Candida, Debaryomyces, Saccharomyces, Pichia, or Hansenula (Japanese Patent Publication No. 4-7195); (2) a method based on the use of a culture liquid or separated microbial cells of a mold belonging to, for example, the genus Stemphylium, Alternaria, Corynespora, or Preussia (Japanese Laid-Open Patent Publication No. 6-38776); (3) a method based on the use of microbial cells of a bacterium belonging to, for example, the genus Brevibacterium, Escherichia, or Lactobacillus, or a yeast belonging to, for example, the genus Kluyveromyces, Saccharomycopsis, or Stephanoascus (Japanese Laid-Open Patent Publication No. 6-209782); and (4) a method based on the use of an enzyme of a yeast or a mold belonging to, for example, the genus Rhodotorula, Fusarium, Paecilomyces, or Verticillium to make a reaction in a two-phase system of water-organic solvent (Japanese Laid-Open Patent Publication No. 63-309195).

However, in any of the production methods described above, there is a limitation on the type of microorganisms which can be used. Certain microogranisms cannot be used since they involve problems in that (1) the reaction velocity is small, and it takes a long time to perform the reaction, (2) the concentration of an accumulated product cannot be increased, and (3) only a product having a low optical purity can be obtained. In view of such circumstances, there is a need to establish a production method which is excellent ecconomically and which makes it possible to produce optically active ester of γ-halogenated-β-hydroxybutyric acid having a high optical purity, at a highly accumulated concentration and at a high yield.

SUMMARY OF THE INVENTION

The present invention has been made taking the foregoing problems into consideration, with the object of providing a method for producing ester of (S)-γ-halogenated-β-hydroxybutyric acid having a high optical purity, the ester being produced in a short period of time of several hours at a highly accumulated concentration and at a high yield.

In order to achieve the object described above, the present inventors have made diligent investigations to develop an efficient method for producing ester of (S)-γ-halogenated-β-hydroxybutyric acid. As a result, it has been found that ester of (S)-γ-halogenated-β-hydroxybutyric acid having a high optical purity can be obtained in a short period of time of several hours at a highly accumulated concentration and at a high yield, by allowing microbial cells and/or a preparation thereof of a microorganism belonging to a specified genus not described in the foregoing respective literatures to act on ester of γ-halogenated acetoacetic acid. Thus, the present invention has been completed.

Namely, the gist of the present invention lies in a method for producing ester of (S)-γ-halogenated-β-hydroxybutyric acid, comprising the steps of:

allowing microbial cells and/or a preparation thereof of a microorganism to act on ester of γ-halogenated-acetoacetic acid represented by the following general formula (I):

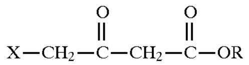

(I)

wherein X represents a halogen atom, and R represents a lower alkyl group; and stereospecifically reducing a carbonyl group located at β-position of the ester of γ-halogenated-acetoacetic acid to produce the ester of (S)-γ-halogenated-β-hydroxybutyric acid represented by the following general formula (II):

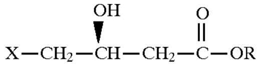

(II)

wherein X and R are synonymous with X and R included in the general formula (I);

the microorganism having an ability to stereospecifically reduce the carbonyl group located at β-position of the ester of γ-halogenated-acetoacetic acid represented by the general formula (I), and being selected from the group consisting of those belonging to the genera Phoma, Nectria, Pseudonectria, Spondylocladium, Melanospora, Metarhizium, Gliocladium, Pestalotia, Pestalotiopsis, Curvularia, Hormonema, Sydowia, Sarcinomyces, Dothiora, Xanthothecium, Dothidea, Pringsheimia, and Selenophoma.

BRIEF DESCRIPTION OF THE DRAWINGS

FIG. 1 shows comparison of nucleotide sequences of 18 S rRNA genes between *Candida albicans* MUCL 29800 (X53497) and various yeast-like fungi, wherein a symbol "." indicates that the nucleotide is the same as that of X53497, and a symbol "-" indicates a gap.

FIG. 2 shows comparison of nucleotide sequences of the 18S rRNA genes between *Candida albicans* MUCL 29800 (X53497) and the various yeast-like fungi, wherein a symbol "." and a symbol "-" are the same as those shown in FIG. 1.

FIG. 3 shows comparison of nucleotide sequences of the 18S rRNA genes between *Candida albicans* MUCL 29800 (X53497) and the various yeast-like fungi, wherein a symbol "." and a symbol "-" are the same as those shown in FIG. 1.

FIG. 4 shows comparison of nucleotide sequences of the 18S rRNA genes between *Candida albicans* MUCL 29800

Figure 10:
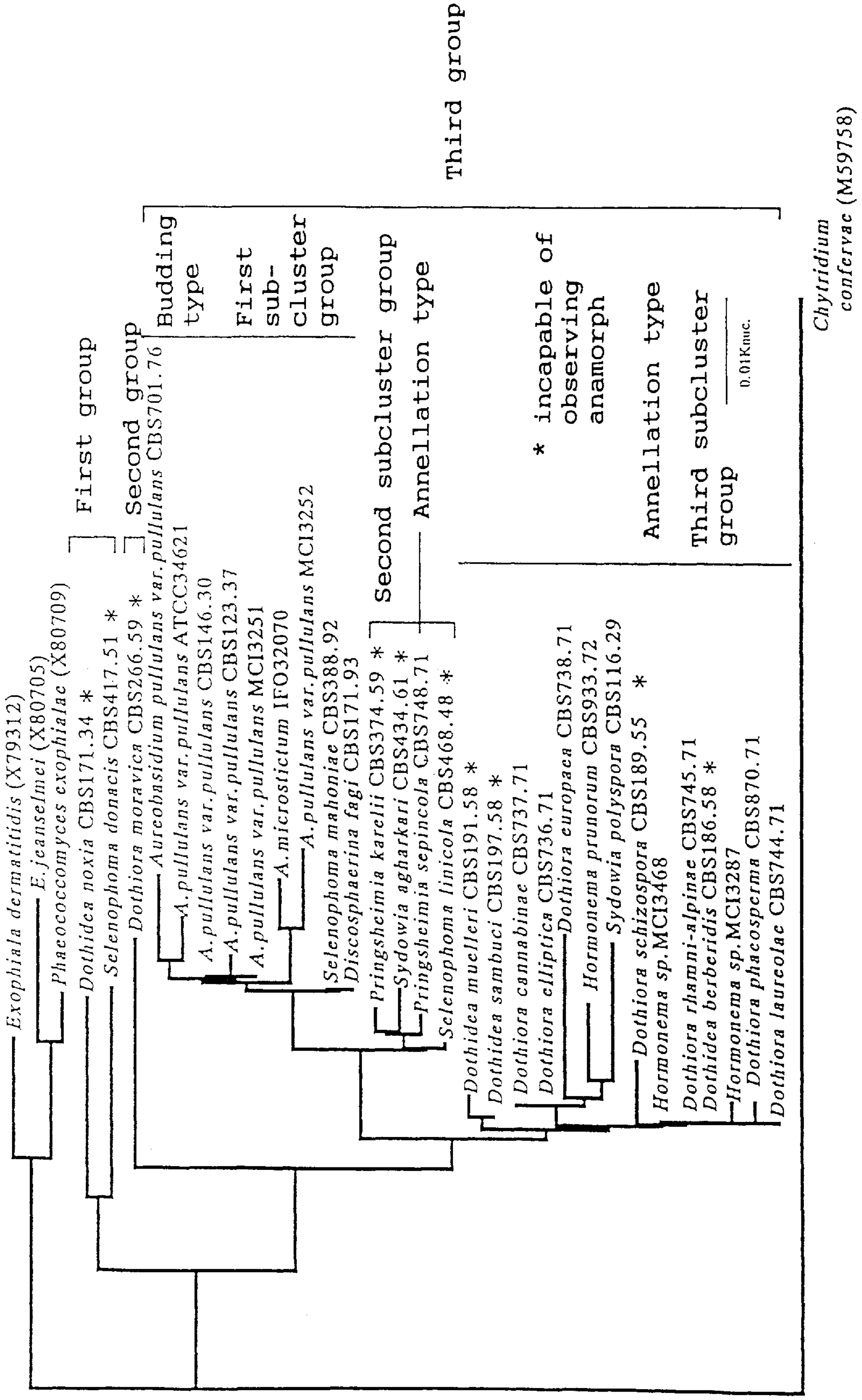

(X53497) and the various yeast-like fungi, wherein a symbol "." and a symbol "-" are the same as those shown in FIG. 1.

FIG. 5 shows comparison of nucleotide sequences of the 18S rRNA genes between *Candida albicans* MUCL 29800 (X53497) and the various yeast-like fungi, wherein a symbol "." and a symbol "-" are the same as those shown in FIG. 1.

FIG. 6 shows comparison of nucleotide sequences of the 18S rRNA genes between *Candida albicans* MUCL 29800 (X53497) and the various yeast-like fungi, wherein a symbol "." and a symbol "-" are the same as those shown in FIG. 1.

FIG. 7 shows comparison of nucleotide sequences of the 18S rRNA genes between *Candida albicans* MUCL 29800 (X53497) and the various yeast-like fungi, wherein a symbol "." and a symbol "-" are the same as those shown in FIG. 1.

FIG. 8 shows comparison of nucleotide sequences of the 18S rRNA genes between *Candida albicans* MUCL 29800 (X53497) and the various yeast-like fungi, wherein a symbol "." and a symbol "-" are the same as those shown in FIG. 1.

FIG. 9 shows comparison of nucleotide sequences of the 18S rRNA genes between *Candida albicans* MUCL 29800 (X53497) and the various yeast-like fungi, wherein a symbol "." and a symbol "-" are the same as those shown in FIG. 1.

FIG. 10 shows a phylogenetic relationship of the yeast-like fungi, based on the partial nucleotide sequences of the 18S rRNA genes.

DESCRIPTION OF THE PREFERRED EMBODIMENTS

The present invention will be described in detail below.

In the production method according to the present invention, the ester of γ-halogenated-acetoacetic acid, represented by the general formula (I), is used as a raw material, on which the microbial cells and/or the preparation thereof of the microorganism belonging to the genus as specified above is allowed to act to produce the ester of (S)-γ-halogenated-β-hydroxybutyric acid represented by the general formula (II).

The halogen atom defined by X in the general formulas (I) and (II) is exemplified by chlorine atom, bromine atom, and iodine atom. Preferably, the halogen atom is exemplified by chlorine atom and bromine atom, and more preferably, the halogen atom is exemplified by chlorine atom.

The lower alkyl group defined by R in the general formulas (I) and (II) is exemplified by lower alkyl groups having a number of carbon atoms of 1 to 4, such as methyl, ethyl, n-propyl, isopropyl, n-butyl, isobutyl, and t-butyl groups. Among the lower alkyl groups, ethyl and methyl groups are preferred, and ethyl group is especially preferred.

<1> Microorganism used in the present invention

The microbial cells and/or the preparation thereof of the microorganism used in the present invention includes microbial cells and/or preparations thereof of microorganisms selected from the group consisting of those belonging to the genera Phoma, Nectria, Pseudonectria, Spondylocladium, Melanospora, Metarhizium, Gliocladium, Pestalotia, Pestalotiopsis, Curvularia, Hormonema, Sydowia, Sarcinomyces, Dothiora, Xanthothecium, Dothidea, Pringsheimia, and Selenophoma. Among them, in view of the productivity of the ester of (S)-γ-halogenated-β-hydroxybutyric acid, the microbial cells and/or the preparation thereof of the microorganism preferably includes those of microorganisms selected from the group consisting of those belonging to the genera Phoma, Spondylocladium, Pestalotia, Curvularia, Hormonema, and Dothiora.

The microorganism used for the production method according to the present invention is not specifically limited provided that it has the ability to act on the carbonyl group at the P-position of the ester of γ-halogenated-acetoacetic acid and stereospecifically reduce (asymmetrically reduce) it. However, those preferably used as the microorganism include, for example, *Phoma sorghina, Nectria lugdunensis, Pseudonectria diparietospora, Spondylocladium xylogenum, Melanospora parasitica, Metarhizium anispoliae, Gliocladium catenulatum, Pestalotia diospyri, Pestalotiopsis funerea, Curvularia fallax*, Hormonema sp., *Hormonema prunorum, Sydowia polyspora, Sarcinomyces crustaceus, Dothiora cannabinae, Dothiora laureolae, Dothiora moravica, Dothiora phaeosperma, Dothiora rhamni-alpinae, Dothiora schizospora, Dothiora elliptica, Dothiora europaea, Xanthothecium peruvianum, Dothidea berberidis, Dothidea muelleri, Dothidea sambuci, Pringsheimia karelii, Pringsheimia sepincola*, and *Selenophoma donacis.*

The microorganisms described above specifically include, for example, the following microbial strains:

*Phoma sorghina* ATCC 13145;
*Nectria lugdunensis* ATCC 16713;
*Pseudonectria diparietospora* ATCC 13214;
*Spondylocladium xylogenum* ATCC 12727;
*Melanospora Parasitica* ATCC 18055;
*Metarhizium anispoliae* IFO 5940;
*Gliocladium catenulatum* IFO 6121;
*Pestalotia diospyri* IFO 5282;
*Pestalotiopsis funerea* IFO 5427;
*Curvularia fallax* IFO 8885;
Hormonema sp. MCI 3287;
*Hormonema prunorum* CBS 933.72;
*Hormonema prunorum* CBS 934.72;
*Hormonema prunorum* CBS 935.72;
*Hormonema prunorum* CBS 765.84;
Hormonema sp. MCI 3468;
*Sydowia polyspora* CBS 116.29;
*Sarcinomyces crustaceus* CBS 156.89;
*Dothiora cannabinae* CBS 737.71;
*Dothiora laureolae* CBS 744.71;
*Dothiora moravica* CBS 266.59;
*Dothiora phaeosperma* CBS 870.71;
*Dothiora rhamni-alpinae* CBS 745.71;
*Dothiora schizospora* CBS 189.55;
*Dothiora elliptica* CBS 736.71;
*Dothiora europaea* CBS 738.71;
*Xanthothecium peruvianum* CBS 301.67;
*Dothidea berberidis* CBS 186.58;
*Dothidea muelleri* CBS 191.58;
*Dothidea sambuci* CBS 197.58;
*Pringsheimia karelii* CBS 374.59;
*Pringsheimia sepincola* CBS 748.71; and
*Selenophoma donacis* CBS 417.51.

The foregoing microorganisms may be any one of strains including, for example, wild strains, mutant strains, and recombinant strains induced by genetic techniques such as cell fusion and genetic recombination methods.

All of the foregoing microbial strains are known except for Hormonema sp. MCI 3287 and Hormonema sp. MCI 3468, and they are easily available from Centraalbureau voor Schimmelcultures (CBS), The American Type Culture Collection (ATCC), and Institute for Fermentation, Osaka (IFO).

Hormonema sp. MCI 3287 and Hormonema sp. MCI 3468 described above are microbial strains which have been newly discovered from nature by the present inventors. Hormonema sp. MCI 3287 has been deposited on May 28, 1996 in National Institute of Bioscience and Human Technology of Agency of Industrial Science and Technology of Ministry of International Trade and Industry under a deposition number of FERM P-15651, transferred to international deposition based on the Budapest Treaty on May 15, 1997, and awarded a deposition number of FERM BP-5945. Hormonema sp. MCI 3468 has been internationally deposited on May 15, 1997 in National Institute of Bioscience and Human Technology of Agency of Industrial Science and Technology of Ministry of International Trade and Industry under a deposition number of FERM BP-5946 based on the Budapest Treaty. The microbiological properties of these microbial strains are shown below.

(1) Hormonema sp. MCI 3287

(i) Morphological nature

The colony grows to a diameter of 2 cm after cultivation at 24° C. for 20 days on potato dextrose agar (PDA) medium.

The colony surface is smooth, initially having a pale yellow brown color. The color subsequently changes to a brown gray color. Aerial hyphae and substrate mycelia develop well at peripheral portions of the colony.

Young hyphae are colorless and branched, and they have septa. The width is 2.8 to 3.8 $\mu$m. Old hyphae undergo a change in color to dark brown. They are thick-walled with a large number of lateral septa, and they are fragmented into hyphal segments at septum portions.

Segmental spores are cylindrical or elliptic, and they are dark brown, each having one or several septa.

Conidiogenous cells are undeveloped, which are spinulose projections branched from hyphae. They appear in a mononematous manner on hyphae or at internodal sections of old brown hyphae.

Conidia are formed in a basipetal manner, exhibiting annello-type conidiogenous. After primary conidia formation, conidia-forming cells are further elongated to form subsequent conidia.

Spinulose projections of conidiogenous cells are elongated in conformity with formation of conidia, and thus an annellation structure is formed. Conidia are elliptic or cylindrical, and they are colorless, each conidium having a size of 5.3 to 12.5×2.2 to 3.8 $\mu$m.

Liberated conidia swell, and they are brown and thick-walled. Each of them usually has one septum, having a size of 12.5 to 15.6×4.1 to 6.3 $\mu$m. No teleomorph was observed.

(ii) Physiological nature

Growth temperature (PDA medium, cultivated for 1 week): 10° to 37° C.;

Optimum growth temperature: 20° to 30° C.;

Growth pH (LCA liquid medium, cultivated for 1 week): 3 to 9;

Optimum growth pH: 6 to 7.

(iii) Taxonomic remarks

The present microbial strain (MCI 3287) exhibit the annello-type conidia formation in which conidia are formed in a basipetal manner from spinulose projection-like conidiogenous cells. Conidiogenous cells previously formed are further elongated to form subsequent conidia. Conidiogenous cells are elongated one after another in conformity with formation of conidia, and thus an annellation structure is formed. As a result of a search at the genus level on the basis of the foregoing nature in accordance with a literature written by E. J. Hermanides-Nijhof, *Stud. Mycol.* 15: 141–181, it has been revealed that the present microbial strain (MCI 3287) belongs to the genus Hormonema.

The genus Hormonema is similar to the genus Aureobasidium in that conidia are formed in a branched manner at internodal sections of hyphae. However, the genus Hormonema exhibits the annello-type conidia formation in which conidia are formed in a basipetal manner. On the other hand, the genus Aureobasidium is characterized in that conidia are formed in an acropetal manner in accordance with yeast-like budding, which can be definitely distinguished from the genus Hormonema.

According to literatures written by Hermanides-Nijhof (1977), *Stud. Mycol.,* 15: 166–177 and G. S. de Hoog & N. A. Yurlova (1994), *Antonie van Leeuwenhoek,* 65: 41–54, the teleomorph of Hormonema includes Discosphaerina, Sydowia, Pringsheimia, Dothiora, and Guignardia belonging to the order Dothideales of the class Loculoascomycetes.

No teleomorph formation was observed for the present microbial strain (MCI 3287).

Therefore, the present microbial strain belongs to the genus Hormonema in the annello-type conidia formation group of the class Hyphomycetes.

According to the literatures written by Hermanides-Nijhof (1977) and G. S. de Hoog & N. A. Yurlova (1994), those belonging to the genus Hormonema in which teleomorph is unclear include *Hormonema dematioides, Hormonema prunorum*, and *Hormonema merioides*. These species are principally distinguished on the basis of the form and the size of conidia.

A research for species was performed in accordance with a key to the species table written by Hermanides-Nijhof. As a result, it has been found that conidia of the present microbial strain have a size of 5.3 to 12.5×2.2 to 3.8 $\mu$m, and hence the present microbial strain is a species similar to *Hormonema dematioides* (*Hormonema merioides:* 4.5 to 12×2.5 to 4.5 $\mu$m).

However, *Hormonema merioides* is characterized in that endoconidia having lateral and longitudinal septa are formed on old hyphae. The present microbial strain has only lateral septa, in which no endoconidia are found. Accordingly, it is judged that the present microbial strain is a microbial species different from Hormonema merioides. Therefore, the present microbial strain (MCI 3287) is estimated to be a new microbial species closely related to *Hormonema merioides*. The name of the species may be determined by further taxonomic investigations expected to be performed in the future. The present microbial strain has been tentatively designated as Hormonema sp. MCI 3287.

(2) Hormonema sp. MCI 3468

(i) Morphological nature

The colony grows to a diameter of 40 mm after cultivation at 24° C. for 7 days on potato dextrose agar (PDA) medium. The colony surface is uniform and smooth, and several stripes of gentle irregularities are formed radially. As the cultivation proceeds, a white mass of spores containing spores and a mass of black viscous liquid are often formed at the center of the colony. A large number of aerial mycelia, which have a shape of short bundle of hyphae, are elongated from central portions of the colony. The surface initially has a cream color, and it changes to an olive color at later stages. The periphery has a cream color, and the back surface of the colony has an olive color with radial wrinkles which are observed corresponding to the surface irregularities. Substrate mycelia are rigidly clustered, giving a leathery form. No characteristic odor is found.

Hyphae are initially colorless and branched, and they have septa. The width is 1.9 to 5.6 $\mu$m. At the later stage of cultivation, walls of hyphae are often thick-walled, providing a dark brown color. The width of the thick-walled hyphae is 3.1 to 7.2 μm. Usually, the width of the cell is shorter than the length of the cell. No septum (longitudinal septum) in the elongation direction is observed.

Conidiogenous cells are undeveloped, forming spinulose projections in many cases, or forming phialide-shaped fairly short branches in some cases. They appear in a mononematous manner from hyphae, in a number of one or two individuals per cell. Conidia are formed in a basipetal manner, in a form of the annello-type conidia formation. Namely, after primary conidia formation, inner walls of conidia-forming cells, which are located just under conidio-liberating surfaces, are elongated to form subsequent conidia. Conidiogenous cells are elongated by repeating the foregoing process, and thus an annellation structure is formed. The annellation structure is unclear when observed by using an optical microscope. However, the structure is clearly confirmed when observed by using a scanning type electron microscope (SEM).

Conidia are elliptic or cylindrical, and they are colorless and unicellular, each conidium having a size of 4.7 to 10.3×1.9 to 4.4 μm. Secondary conidia are sometimes formed. Liberated conidia often swell, and they become thick-walled. Most of them are bicellular. They are brown, and they have a size of 6.3 to 12.2×3.1 to 6.6 μm.

Neither endoconidia nor teleomorph was observed.

(ii) Physiological nature

Growth temperature (on PDA, cultivated for 7 days): 10° to 30° C.;

Optimum growth temperature: 20° C.;

Growth pH (in LCA liquid medium, cultivated for 10 days): 3 to 10;

Optimum growth pH: 6 to 7.

(iii) Taxonomic remarks

The present microbial strain (MCI 3468) is characterized in that 1) it has no teleomorph, 2) conidiogenous cells have a shape of spinulose projection, 3) conidia are formed from conidiogenous cells in a basipetal manner, and 3) the form of conidia formation is the annello-type with the annellation structure formed at the tip of conidiogenous cells. As a result of a search at the genus level on the basis of the foregoing nature in accordance with a key to the genera in a literature written by E. J. Hermanides-Nijhof (1977), *Study in Mycology,* 15: 141–181, it has been revealed that the present m icrobial strain (MCI 3468) belongs to the genus Hormonema. The genus Hormonema is similar to the genus Aureobasidium in that conidia are formed in a branched manner at internodal sections of hyphae. However, in the case of those belonging to the genus Aureobasidium, several conidia synchronously bud around internodal sections of hyphae, while in the case of those belonging to the genus Hormonema, conidia are usually formed in a basipetal manner from one or two sites per one cell, exhibiting the annello-type conidia formation process. Therefore, the former can be clearly distinguished from the latter. According to E. J. Hermanides-Nijhof (1977), *Study in Mycology,* 15: 166–177 and G. S. de Hoog & N. A. Yurlova (1994), *Antonie van Leeuwenhoek,* 65: 41–54, the teleomorph of the genus Hormonema includes the genera Discosphaerina, Sydowia, Pringsheimia, Dothiora, and Guignardia belonging to the order Dothideales of the class Loculoascomycetes. The teleomorph formation was not observed for the present microbial strain (MCI 3468). Therefore, the present microbial strain belongs to the genus Hormonema in the annello-type conidia formation group of the class Hyphomycetes of the subphylum Deuteromycotina.

According to the literatures written by E. J. Hermanides-Nijhof (1977), Funk, A., T. A. D. Woods and S. J. Hopkinson (1985), and G. S. de Hoog & N. A. Yurlova (1994), three species are described as microorganisms belonging to the genus Hormonema. These species are principally distinguished on the basis of the form of conidia and the growth speed. As a result of identification for the species based on the foregoing literatures, it has been revealed that the present microbial strain is a species similar to Hormonema dematioides. Principal morphological features are compared in Table 1 for the present microbial strain and *Hormonema dematioides* (information in the literature written by E. J. Hemmanides-Nijhof (1977)).

As shown in Table 1, for example, *Hormonema merioides* is characterized in that thickened hyphae have lateral and vertical septa, endoconidia are formed, and the optimum growth temperature is 24° C. However, the present microbial strain is different from *Hormonema merioides* in that it has only lateral septa, no endoconidia formation is found, and the optimum growth temperature is 24° C. Accordingly, it is judged that the present microbial strain is a microbial species different from *Hormonema merioides*. Therefore, the present microbial strain (MCI 3468) is estimated to be a new microbial species closely related to *Hormonema merioides*. The name of the species may be determined by further taxonomic investigations expected to be performed the future. The present microbial strain has been tentatively designated as Hormonema sp. MCI 3468.

TABLE 1

Comparison for Principal Characters

| | MCI 3468 | *H. dematioides* |
|---|---|---|
| Growth (24° C., 7 days) | 40 mm | 50 to 60 mm |
| Optimum growth temp. | 20° C. | 24° C. |
| Colony | | |
| Surface | smooth | smooth |
| Color | pale olive | gray or olive |
| Texture | rigid (leathery) | rigid (leathery) |
| Hypha | | |
| Width (μm) | 1.9 to 5.6 | 3 to 13 |
| Shape* | L > W | L < W |
| Vertical septum | absent | present |
| Conidiogenous cell | undifferentiated | undifferentiated |
| Annellation | present | present |
| Conidia | | |
| Size (μm) | 4.4–8.1 × 1.9–3.1 | 4.5–12.0 × 2.5–4.5 |
| Thick-walled state | present | present |
| Endoconidia | absent | present |

*L > W: cell length is longer than hyphal width;
L < W: cell length is shorter than hyphal width in some cells.

<2> Taxonomic investigations on microorganisms used for the present invention (1) Classification and identification based on the use of sequence of 18S ribosomal RNA gene In the 1980s, the molecular systematics for studying phylogenetic relationships and systematic evolution of organisms at the molecular level came into existence owing to the progress of the technology in molecular biology, especially the cloning techniques, the PCR (Polymerase Chain Reaction) method, the development of automatic sequencers, the popularization of computers capable of high-speed operation, and the development of new programs for analyzing molecular evolution. In the molecular evolution process, change occurs at an approximately constant speed as compared with change in morphology. Accordingly, it is considered that such a process may be regarded as "molecular clock", and the phylogenetic relationship between organisms can be estimated by making comparison for informational macromolecules such as DNA, RNA, and proteins of organisms. In the field of fungi and molds, there has been adopted the technique for analyzing nucleotide sequence of ribosomal RNA. Data are being accumulated principally for yeasts and yeast-like fungi as well as for a part of other molds.

In 1980, P. M. Rubtsov et al. determined a nucleotide sequence of 18S ribosomal RNA (hereinafter referred to as "18S rRNA") of *Saccharomyces cerevisiae. Nucleotide sequences of* 18S rRNA were reported, for example, in 1989 for *Candida albicans* (L. Hendriks et al., *Syst. Appl. Microbiol.* 12: 223–229), in 1995 for Yeast-like fungi (G. Haase et al., Antonie van Leeuwenhoek 68: 19–35), and in 1995 for Yeast-like fungi (C. P. Kurtzman & C. J. Robnett, Can. J. Bot. 73: S824–S830).

In such a circumstance, the present study has been made in order that 1) the phylogenetic relationship among yeast-like fungi, including microbial strains described in production examples of the present invention, is clarified by means of comparative analysis for nucleotide sequences of 18S rRNA genes and used as an excellent indicator for estimating the molecular phylogenetic relationships, and 2) yeast-like fungi are classified from both viewpoints of morphology and obtained molecular information (nucleotide sequences of 18S rRNA genes). The following 30 microbial strains were used to analyze nucleotide sequences of 18S rRNA.

[Analyzed microbial strains]

*Aureobasidium microstictum* IFO 32070;
*Aureobasidium pullulans* var *pullulans* CBS 701.76;
*Aureobasidium pullulans* var *pullulans* ATCC 34621;
*Aureobasidium pullulans* var *pullulans* CBS 146.30;
*Aureobasidium pullulans* var *pullulans* CBS 123.37;
*Aureobasidium pullulans* var *pullulans* MCI 3251;
*Aureobasidium pullulans* var *pullulans* MCI 3252;
*Discosphaerina faqi* CBS 171.93;
*Dothidea berberidis* CBS 186.58;
*Dothidea noxia* CBS 171.34;
*Dothidea muelleri* CBS 191.58;
*Dothidea sambuci* CBS 197.58;
*Dothiora cannabinae* CBS 737.71;
*Dothiora elliptica* CBS 736.71;
*Dothiora europaea* CBS 738.71;
*Dothiora laureolae* CBS 744.71;
*Dothiora moravica* CBS 266.59;
*Dothiora phaeosperma* CBS 870.71;
*Dothiora rhamni-alpinae* CBS 745.71;
*Dothiora schizospora* CBS 189.55;
*Hormonema prunorum* CBS 933.72;
Hormonema sp. MCI 3287;
Hormonema sp. MCI 3468;
*Pringsheimia karelii* CBS 374.59;
*Pringsheimia sepincola* CBS 748.71;
*Selenophoma donacis* CBS 417.51;
*Selenophoma linicola* CBS 468.48;
*Selenophoma mahoniae* CBS 388.92;
*Sydowia agharkari* CBS 434.61;
*Sydowia polyspora* CBS 116.29.

[Experimental method]

Malt medium (malt powder 20 g, polypeptone 1 g, glucose 20 g, and desalted water 1 L) was charged in an amount of 40 ml to a Erlenmeyer flask having a volume of 200 ml, and sterilized by means of autoclave. After which, each of the microbial strains was inoculated to the flask to perform cultivation with shaking at 150 rpm for 4 to 10 days at 20° C. or at 24° C. Upon the cultivation, one flask was used for one microbial strain. Cultivated microbial cells were collected by filtration with a filter (Toyo Filter Paper No. 101).

Fungal DNA was extracted and purified in accordance with a method described by Yotsumoto, Ohara, and Mikawa (1995) *Microbial. Cult. Coll.* 11: 19–21. 18S rRNA gene was amplified, cloned, and purified principally in accordance with a protocol of D. M. Hills et al. (1996) *Molecular Systematics,* 2nd ed. pp. 205–381. Sinauer. DNA was extracted and purified from frozen wet microbial cells to perform PCR in the presence of Taq polymerase and two synthetic primers (5'-CTACTGCGAAAGCATTTGCCAAGG-3' (SEQ ID NO: 56), 5'-GAGGAAGTAAAAGTCGTAACAAGG-3' (SEQ ID NO: 57)) having complementarity to positions corresponding to nucleotide numbers 917 to 940 and 1733 to 1756 as counted from the 5'-terminal of a nucleotide sequence of 18S rRNA of Candida albicans (L. Hendriks et al. 1989, *System. Appl. Microbiol.* 12: 223–229). Thus a partial nucleotide sequence (941 to 1732) of a gene (18S rDNA) coding for 18S rRNA was amplified.

The amplified DNA fragment was purified by means of acrylamide gel electrophoresis to recover a rDNA fragment which was incorporated into pT7 vector, and *Escherichia coli* was transformed therewith to determine the nucleotide sequence by means of the dideoxy method. Sequencing was performed in accordance with a manual provided by ABI. High sensitivity automatic sequencer ABI 377 produced by ABI was used as a sequencer.

Obtained sequence data were edited by using Gene Analysis Software GENETYX-MAC (produced by Software Development), and alignment was made by using Nucleotide Data Alignment Software CLUSTAL W (J. D. Thompson et al., 1994, *Nucl. Acid Res.* 22: 4673–4680). A phylogenetic tree was prepared in accordance with the neighbour-joining method by using Phylogenetic Tree-Preparing Package Software, Phylip (J. Felsenstein. PHYLIP-Phylogenetic inference package, version 3.5 C, Computer programs distributed by the author, Department of Genetics, Univ. of Washington, Seattle).

In order to make reference for systematic analysis, nucleotide sequences of the following microorganisms registered in data bank were utilized: *Candida albicans* X53497, *Chytridium confervae* M59758, *Exophiala dermatitidis* X79312, *Exophiala jeanselmei* X80705, and *Phaeococcomyces exophialae* X80709. The numbers affixed after the microbial names indicate accession numbers of nucleotide sequences of 18S rRNA genes registered in EMBL (European Bioinformatics Institute) and GenBank (National Center for Biotechnology Information). For example, X53497 indicates a nucleotide sequence of 18S rRNA of *Candida albicans.*

[Result]

FIGS. 1 to 9 show alignments of partial nucleotide sequences of 18S rRNA genes of yeast-like fungi including microbial strains referred to in Examples described later on. The nucleotide sequences of the 18S rRNA genes of the analyzed microbial strains are arranged complementarily to the sequence of *Candida albicans* X53497. The entire nucleotide sequence of *Candida albicans* X53497 is shown in SEQ ID NO: 1 in Sequence Listing. Nucleotide sequences of portions corresponding to nucleotide numbers of 1117 to 1631 of X53497, of partial nucleotide sequences of 18S rRNA genes of the respective analyzed microbial strains, are shown in SEQ ID NOs: 1 to 31 in Sequence Listing. Nucleotide numbers of 1480 to 1498 defined in claims concern portions corresponding to nucleotide numbers of 1478 to 1498 and 1578 to 1590 of the nucleotide sequence of *Candida albicans* X53497 shown in SEQ ID NO: 1 respectively.

As a result of comparison of the nucleotide sequences of the 18S rRNA genes of *Candida albicans* X53497 and the respective analyzed microbial strains, the two portions described above (1480 to 1498 and 1579 to 1591) included conservative and variable regions as compared with other portions. Therefore, it was judged that the two portions could be used as appropriate materials for phylogenetic systematics.

FIG. 10 shows a phylogenetic tree of the respective yeast-like fungi, prepared in accordance with the neighbour-joining method on the basis of the nucleotide sequences of the 18S rRNA genes determined as described above. As shown in the phylogenetic tree, the analyzed 30 microbial strains were roughly classified into three clusters (first, second, and third groups).

The first group comprises *Dothidea noxia* and *Selenophoma donacis*. The second group comprises *Dothiora moravica.*

The third group comprises the microbial species belonging to the genera Aureobasidium and Dothiora. The third group is further divided into three subclusters (first, second, and third subcluster groups). The first subcluster group principally includes the microbial species belonging to the genus Aureobasidium as well as *Selenophoma mahoniae* and *Discosphaerina fagi*. The second subcluster group comprises *Pringsheimia karelii, Pringsheimia sepincola, Sydowia agharkari*, and *Selenophoma linicola*. The third subcluster group comprises *Dothidea muelleri, Dothidea sambuci, Dothidea berberidis, Dothiora schizospora, Dothiora cannabinae, Dothiora elliptica, Dothiora europaea, Dothiora rhamni-alpinae, Dothiora phaeosperma, Dothiora laureolae, Sydowia polyspora, Hormonema prunorum*, and Hormonema spp. (MCI 3287, MCI 3468).

(2) Molecular systematic investigations

According to the result of phylogenetic analysis of 18S rRNA, it is considered that the genera Dothidea, Dothiora, Selenophoma, and Sydowia comprise phylogenetically different species groups, and it is necessary to reorganize the foregoing genera from a taxonomic viewpoint. As for the third group, the yeast-like fungi belonging to the genera Aureobasidium and Hormonema included in the first and third subcluster groups are those concerning anamorph genera related to, for example, Dothidea, Dothiora, Discosphaerina, and Pringsheimia belonging to Dothideales of the class Loculoascomycetes (Hermanides-Nijhof, 1977; Sivanesan, 1984; Hawksworth, 1994).

Those belonging to the genus Aureobasidium form conidia in an acropetal manner from side surfaces of hyphae through the process of synchronous budding, which are distinguished from those belonging to the genus Hormonema which principally exhibit annellation type conidia formation. However, it is sometimes difficult to distinguish conidia of the budding type from those of the annellation type. Both types exist in a mixed manner in some microbial strains. Therefore, there is a situation in which the classification of both genera is confusing (Hermanides-Nijhof, 1977; Sivanesan, 1984; Hawksworth, 1994). As shown in FIG. 10, according to the results of classification and identification based on the sequences of the 18S rRNA genes described above, it has been revealed that those belonging to the genera Aureobasidium and Hormonema are divided into two phylogenetic groups respectively, corresponding to the mode of formation of conidia. According to this fact, it has been suggested that the mode of formation of conidia is a taxonomic character which reflects the phyletic line.

Those belonging to the genera Dothidea, Dothiora, and Sydowia of the teleomorph genera constitute the third subcluster group in the vicinity of those belonging to the genus Hormonema having the annellation type conidia. In order to confirm the type of conidia formation, the microbial strains of these genera were cultivated at 20° C. for 2 weeks on PDA medium and LCA medium to carefully investigate the conidia formation by using a scanning type electron microscope. It was revealed that *Dothiora cannabinae, Dothiora elliptica, Dothiora europaea, Dothiora rhamni-alpinae, Dothiora phaeosperma, Dothiora laureolae*, and *Sydowia polyspora* had definite annellation type conidia. Among them, *Dothiora cannabinae, Dothiora elliptica, Dothiora phaeosperma*, and *Dothiora rhamni-alpinae* had a completely coincident nucleotide sequence of 500 bp analyzed in the present experiment, and they had a common property that they formed annellation type conidia. According to these facts, they were assumed to belong to a phylogenetically identical species group.

It was strongly suggested that the microbial strains of Hormonema spp. (MCI 13287, MCI 13468), which were newly isolated by the present study, were of the anamorph related to species belonging to the genus Dothiora described above. Those of the telemorph genera, in which conidia formation was not observed in the third subcluster group, included *Dothidea muelleri, Dothidea sambuci, Dothidea berberidis*, and *Dothidea schizospora*. It is postulated that the group of these microbial strains are microbial species deficient in the anamorph generation. However, it is suggested from the result of nucleotide sequencing that they phylogenetically belong to the same species group as that of the group of microbial strains which have the anamorph of those belonging to the genus Hormonema.

Those belonging to the genus Selenophoma concern those of the anamorph genus which form pycnidia. However, as shown in FIG. 10, they do not form any consistent phylogenetic branch as a result of the analysis for the genes, and hence those belonging to this genus may require taxonomic reorganization. *Selenophoma mahoniae* and *Discosphaerina fagi* form an identical phylogenetic branch, revealing that the former belongs to the genus related to the anamorph of Discosphaerina. The mode of conidia formation was observed for those belonging to the genera Discosphaerina and Selenophoma. As a result, it was strongly supported that both *Discosphaerina fagi* and *Selenophoma mahoniae* formed budding type conidia, and that the microorganisms belonging to both genera were morphologically in a relationship of teleomorph and anamorph. On the other hand, conidia could not be observed for *Selenophoma donacis* and *Selenophoma linicola.*

*Pringsheimia karelii, Pringsheimia sepincola*, and *Sydowia agharkari* formed one phylogenetic branch (second subcluster group). A species belonging to the genus Sydowia was also distributed in the third subcluster group in a scattered manner. Accordingly, it was suggested that the genus Sydowia was phylogenetically heterogeneous. As a result of observation for the mode of conidia formation, *Pringsheimia sepincola* formed annellation type conidia. However, conidia were not observed for *Pringsheimia karelii* and *Sydowia agharkari.*

It was strongly suggested that the nucleotide sequence of the 18S rRNA gene was effective as an indicator for verifying the relationships of anamorph-teleomorph. It was also found that the nucleotide sequence of the 18S rRNA gene might provide objective information for reconstructing the classification system of the teleomorph genus on the basis of the form of fruit bodies.

Table 2 shows classification of the yeast-like fungi, based on spore formation and the nucleotide sequences of the 18S rRNA genes of the portions corresponding to those of 1480 to 1498 and 1579 to 1591 of *Candida albicans* X53497. It is strongly suggested that microorganisms which are classified into this table, i.e., microorganisms which belong to the identical genera, which have the same spore-forming properties, and which have the same nucleotide sequence at the foregoing portion of the 18S rRNA gene, have the ability to stereospecifically reduce the carbonyl group located at β-position of the ester of γ-halogenated-acetoacetic acid represented by the general formula (I) described above, in the same manner as the respective microbial strains used in Examples described later on, and thus they can be used for the method of the present invention.

TABLE 2

| Microbial name | Spore formation | 18S rRNA sequence (SEQ ID NO) 1480–1498 | 1579–1591 |
|---|---|---|---|
| *Dothiora cannabinae* *D. elliptica* *D. phaeosperma* *D. rhamni-alpinae* *Hormonema sp.* MCI 3287 *Hormonema sp.* MCI 3468 | annellation type spore formed | 32 | 33 |
| *Dothiora europaea* | annellation type spore formed | 34 | 35 |
| *Dothiora laureolae* | annellation type spore formed | 36 | 37 |
| *Dothiora schizospora* | no spore formed | 38 | 39 |
| *Hormonema prunorum* | annellation type spore formed | 40 | 41 |
| *Sydowia polyspora* | annellation type spore formed | 42 | 43 |
| *Pringsheimia sepincola* | annellation type spore formed | 44 | 45 |
| *Dothidea muelleri* *Dothidea sambuci* | no spore formed | 46 | 47 |
| *Selenophoma donacis* | no spore formed | 48 | 49 |
| *Dothiora moravica* | no spore formed | 50 | 51 |
| *Pringsheimia karelii* | no spore formed | 52 | 53 |
| *Dothidea berberidis* | no spore formed | 54 | 55 |

<3> Method for producing ester of (S)-γ-halogenated-β-hydroxybutyric acid

The production method according to the present invention uses one or more microorganisms having the ability to act on the carbonyl group located at the β-position of the ester of γ-halogenated-acetoacetic acid described above and stereospecifically reduce (asymmetrically reduce) it, in a form of the microbial cells and/or the preparation thereof. Specifically, those usable in the present invention include, for example, microbial cells as they are obtained by cultivating the microorganism described above, a preparation obtained by treating, with acetone, microbial cells obtained by cultivation, a preparation obtained by lyophilizing microbial cells, and a preparation obtained by mechanically or enzymatically disrupting microbial cells. It is also possible to extract and use, from the microbial cells or the preparation, an enzyme fraction having the ability to act on the carbonyl group located at the β-position of the ester of γ-halogenated-acetoacetic acid represented by the foregoing general formula (I) and stereospecifically reduce (asymmetrically reduce) and convert it into the ester of (S)-γ-halogenated-β-hydroxybutyric acid represented by the foregoing general formula (II), as a crude preparation or a purified preparation. Further, it is also possible to use those obtained by immobilizing the microbial cells, the preparation, the enzyme fraction or the like to a carrier such as polyacrylamide gel and carageenan gel. In this specification, the term "microbial cells and/or preparation thereof" is used as a concept which includes all of the microbial cells, the preparation, the enzyme fraction, and the immobilized preparation thereof as described above.

The method for producing the ester of (S)-γ-halogenated-β-hydroxybutyric acid of the present invention will be specifically explained below.

In the production method of the present invention, the ester of γ-halogenated-acetoacetic acid represented by the foregoing general formula (I) is used as a raw material, on which the microbial cells and/or the preparation thereof of the microorganism belonging to the specified genus described above is allowed to act to produce the ester of (S)-γ-halogenated-β-hydroxybutyric acid represented by the foregoing general formula (II).

In the production method of the present invention, the microorganism is usually used after cultivation. The cultivation can be performed in accordance with an ordinary method. The medium used for cultivation may include those containing, in an appropriate combination, a carbon source such as glucose, sucrose, glycerol, and citric acid; an inorganic nitrogen source such as ammonium sulfate and sodium nitrate; an organic nitrogen source such as yeast extract, peptone, urea, meat extract, and corn steep liquor; inorganic salts such as those of magnesium and potassium; and phosphoric acid. Other than these components, it is also possible to add inorganic salts, trace metals, amino acids, and vitamins, as substances to facilitate the reaction activity. Preferably, the cultivation is performed while adjusting pH of the medium in a range of 3 to 10 at a temperature of 10° to 45° C. for a period of time in a range of 1 to 10 days until the activity is maximized.

In the present invention, the microbial cells and/or the preparation thereof of the microorganism obtained by performing the cultivation, as described above, is allowed to contact, in an aqueous medium, with the ester of γ-halogenated-acetoacetic acid represented by the foregoing general formula (I) to make the reaction so that the ester of (S)-γ-halogenated-β-hydroxybutyric acid represented by the foregoing general formula (II) is obtained as the reaction product. The aqueous medium used herein includes, for example, water, buffer, and culture liquid. However, the aqueous medium may contain water-soluble organic solvent or oil-soluble organic solvent, if necessary. When the reaction is performed, the yield is clearly improved by adding, to the reaction solution, glucose, sucrose, fructose, ethanol, and/or methanol, as an energy source.

In the ester of γ-halogenated-acetoacetic acid used in the present invention, chlorine is preferred as halogen, and ethyl ester is preferred as ester. Ethyl (S)-γ-chloro-β-hydroxybutyrate is especially preferred.

The ester of γ-halogenated-acetoacetic acid is added to the reaction solution in an amount which renders the concentration of the ester in the reaction solution to about 0.01 to 50% by weight. It is not necessarily indispensable that the added ester of γ-halogenated-acetoacetic acid is completely dissolved in the aqueous medium in the reaction solution. When the reaction suffers substrate inhibition, the amount of accumulated product can be further increased by continuously or intermittently adding, in an amount corresponding to consumption, the ester of γ-halogenated-acetoacetic acid which is consumed as the reaction proceeds. The microbial cells and/or the preparation thereof of the microorganism is added to the reaction solution as follows. When the microbial cells are added, they are added to the reaction solution so that the concentration of the microbial cells is about 0.01 to 20% by weight. When the preparation such as the enzyme is used, the specific activity of the enzyme is determined, and the preparation is added in an amount so that the enzyme concentration obtained after addition corresponds to the concentration of the microbial cells described above. Preferred reaction conditions are as follows. Namely, the reaction temperature is from the freezing point to 70° C., preferably 10° to 40° C., pH is 2 to 11, preferably 5 to 8, and the reaction time is about 1 to 100 hours.

In accordance with the reaction as described above, the ester of (S)-γ-halogenated-β-hydroxybutyric acid is obtained as the reaction product. The method for isolating, from the reaction solution, the optically active ester of (S)-γ-halogenated-β-hydroxybutyric acid as the objective product includes, for example, a method comprising the steps of removing the microbial cells and/or the preparation thereof by means of centrifugation, extracting from the reaction solution the ester of (S)-γ-halogenated-β-hydroxybutyric acid with an organic solvent such as chloroform and ethyl acetate, and isolating the ester by utilizing known methods such as distillation and column chromatography.

According to the production method of the present invention, the ester of (S)-γ-halogenated-β-hydroxybutyric acid having a high optical purity can be produced in a short period of time of several hours at a high yield and at a highly accumulated concentration, which is extremely advantageous from the industrial viewpoint.

DESCRIPTION OF PREFERRED EMBODIMENTS

Examples of the present invention will be explained below.

EXAMPLE 1

Microbial cells of various microorganisms shown in Table 3 were inoculated to a 100 ml medium containing 4.0% glucose, 2.0% yeast extract, and 0.5% corn steep liquor (pH 6.0) respectively to perform cultivation aerobically with shaking at 26° C. for 2 to 5 days (cultivation was performed at 21° C. for microorganisms affixed with symbol * in Table 3). After completion of cultivation, microbial cells were collected by means of centrifugation, and washed with phosphate buffer (0.1M, pH 6.5). After which, the respective microbial cells were suspended in 100 ml of the same buffer containing 3.0% glucose so that the concentration of the microbial cells was the same as that in the liquid culture. Ethyl γ-chloroacetoacetate was added to each of the microbial cell suspensions respectively in an amount of 2.0 g to perform a reaction with shaking at 26° C. for 4 hours.

After completion of the reaction, the microbial cells were removed from each of the reaction solutions by means of centrifugation to obtain a reaction supernatant which was subjected to reverse phase HPLC analysis [Cosmosil 5C18; eluent: 20% acetonitrile aqueous solution; flow rate: 1.0 ml/minute; UV: 220 nm]. Thus, the amount of produced ethyl (S)-γ-chloro-β-hydroxybutyrate was determined. One hundred ml of ethyl acetate was added to each of the reaction supernatants to perform extraction followed by concentration, and an obtained extract was dissolved in isopropanol to measure the optical purity and determine the absolute configuration by means of optical resolution HPLC analysis [column: Daicel CHIRALCEL OD; eluent: hexane/isopropanol=9/2; flow rate: 0.5 ml/minute; detection: RI]. Obtained results are shown in Table 3. The production amount shown in Table 3 indicates an amount of produced product calculated and expressed as an amount per culture liquid (unit: g/L/broth).

TABLE 3

| Microbial name | Production amount [g/L/broth] | Optical purity [% e.e.] | Absolute configuration |
|---|---|---|---|
| *Phoma sorghina* ATCC 13145 | 17 | 98.5 | S |
| *Nectria lugdunensis* ATCC 16713 | 18 | 93.2 | S |
| *Pseudonectria diparietospora* ATCC 13214 | 18 | 93.5 | S |
| *Spondylocladium xylogenum* ATCC 12727 | 17 | 97.5 | S |
| *Melanospora parasitica* ATCC 18055 | 19 | 92.1 | S |
| *Metarhizium anispoliae* IFO 5940 | 17 | 93.5 | S |
| *Gliocladium catenulatum* IFO 6121 | 19 | 92.4 | S |
| *Pestalotia diospyri* IFO 5282 | 18 | 97.8 | S |
| *Pestalotiopsis funerea* IFO 5427 | 18 | 94.1 | S |
| *Curvularia fallax* IFO 8885 | 19 | 97.0 | S |
| *Hormonema sp.* MCI 3287 | 19 | 97.0 | S |
| *Hormonema prunorum* CBS 933.72 | 12 | 96.2 | S |
| *Hormonema prunorum* CBS 934.72 | 12 | 96.5 | S |
| *Hormonema prunorum* CBS 935.72 | 13 | 94.4 | S |
| *Hormonema prunorum* CBS 765.84 | 14 | 97.1 | S |
| *Hormonema sp.* MCI 3468 | 19 | 99.6 | S |
| *Sydowia polyspora* CBS 116.29 | 14 | 96.5 | S |
| *Sarcinomyces crustaceus* CBS 156.89 | 14 | 95.8 | S |
| *Dothiora cannabinae* CBS 737.71 | 17 | 97.7 | S |
| *Dothiora laureolae* CBS 744.71 | 13 | 97.5 | S |
| *Dothiora moravica* CBS 266.59 | 14 | 98.1 | S |
| *Dothiora phaeosperma* CBS 870.71* | 15 | 99.4 | S |
| *Dothiora rhamni-alpinae* CBS 745.71* | 16 | 97.1 | S |
| *Dothiora schizospora* CBS 189.55 | 14 | 95.4 | S |
| *Dothiora elliptica* CBS 736.71* | 15 | 99.8 | S |
| *Dothiora europaea* CBS 738.71* | 17 | 98.1 | S |
| *Xanthothecium peruvianum* CBS 301.67 | 14 | 94.2 | S |
| *Dothidea berberidis* CBS 186.58 | 16 | 92.1 | S |
| *Dothidea muelleri* CBS 191.58* | 16 | 94.7 | S |
| *Dothidea sambuci* CBS 197.58* | 11 | 96.3 | S |
| *Pringsheimia karelii* CBS 374.59 | 16 | 97.6 | S |
| *Pringsheimia sepincola* CBS 748.71 | 11 | 97.5 | S |
| *Selenophoma donacis* CBS 417.51 | 16 | 95.3 | S |

[Cultivation temperature was 21° C. for microbial strains with *.]

EXAMPLE 2

Microbial cells of Hormonema sp. MCI 3287 was used and methyl γ-chloroacetoacetate was used as the reaction substrate to produce methyl (S)-γ-chloro-β-hydroxybutyrate in accordance with the same procedure as that used in Example 1. The production amount and the optical purity of methyl (S)-γ-chloro-β-hydroxybutyrate obtained by this reaction were measured in accordance with the same method as that used in Example 1 described above. As a result, the production amount was 19 g/L/broth, and the optical purity was 95.0% e.e. (S) enantiomer.

EXAMPLE 3

Microbial cells of Hormonema sp. MCI 3287 was used and ethyl γ-bromoacetoacetate was used as the reaction substrate to produce ethyl (S)-γ-bromo-β-hydroxybutyrate in accordance with the same procedure as that used in Example 1. The production amount and the optical purity of ethyl (S)-γ-bromo-β-hydroxybutyrate obtained by this reaction were measured in accordance with the same method as that used in Example 1 described above. As a result, the production amount was 16 g/L/broth, and the optical purity was 97.2% e.e. (S) enantiomer.

EXAMPLE 4

Microbial cells of Hormonema sp. MCI 3287 were inoculated to a 100 ml medium containing 4.0% glucose, 2.0% yeast extract, and 0.5% corn steep liquor (pH 6.0) to perform cultivation aerobically with shaking at 26° C. for 2 days. After completion of cultivation, microbial cells were collected by means of centrifugation, and washed with phosphate buffer (0.1M, pH 6.5). After which, the microbial cells were suspended in 100 ml of the same buffer containing 3.0% glucose so that the concentration of the microbial cells was the same as that in the liquid culture. Ethyl γ-chloroacetoacetate was added to the microbial cell suspension in a total amount of 3.5 g while maintaining pH 6.3 with 1M $Na_2CO_3$ aqueous solution to perform a reaction with stirring at 26° C. for 8 hours.

After completion of the reaction, the production amount and the optical purity of obtained ethyl (S)-γ-chloro-β-hydroxybutyrate were measured in accordance with the same method as that used in Example 1 described above. As a result, the production amount was 32 g/L/broth, and the optical purity was 97.5% e.e. (S) enantiomer.

EXAMPLE 5

Microbial cells of Hormonema sp. MCI 3468 were used so that production of ethyl (S)-γ-chloro-β-hydroxybutyrate was carried out in accordance with the same procedure as that used in Example 4.

After completion of the reaction, the production amount and the optical purity of obtained ethyl (S)-γ-chloro-β-hydroxybutyrate were measured in accordance with the same method as that used in Example 1 described above. As a result, the production amount was 34 g/L/broth, and the optical purity was 99.0% e.e. (S) enantiomer.

It is understood from the foregoing results that the production method according to the present invention makes it possible to produce the ester of (S)-γ-halogenated-β-hydroxybutyric acid having a high optical purity in a short period of time of several hours at a high yield and at a highly accumulated concentration.

---

What is claimed is:

1. A method for producing ester of (S)-γ-halogenated-β-hydroxybutyric acid, comprising the steps of:

allowing microbial cells and/or a preparation thereof of a microorganism to act on ester of γ-halogenated-acetoacetic acid represented by the following general formula (I):

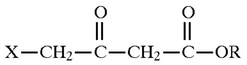
(I)

wherein X represents a halogen atom, and R represents a lower alkyl group; and stereospecifically reducing a carbonyl group located at β-position of the ester of γ-halogenated-acetoacetic acid to produce the ester of (S)-γ-halogenated-β-hydroxybutyric acid represented by the following general formula (II):

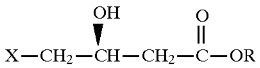
(II)

wherein X and R are synonymous with X and R included in the general formula (I);

the microorganism having an ability to stereospecifically reduce the carbonyl group located at β-position of the ester of γ-halogenated-acetoacetic acid represented by the general formula (I), and being selected from the group consisting of microorganisms belonging to the genera Phoma, Nectria, Pseudonectria, Spondylocladium, Melanospora, Metarhizium, Gliocladium, Pestalotia, Pestalotiopsis, Curvularia, Hormonema, Sydowia, Sarcinomyces, Dothiora, Xanthothecium, Dothidea, Pringsheimia, and Selenophoma.

2. The method according to claim 1, wherein the microorganism belongs to the genus Phoma.

3. The method according to claim 1, wherein the microorganism belongs to the genus Spondylocladium.

4. The method according to claim 1, wherein the microorganism belongs to the genus Pestalotia.

5. The method according to claim 1, wherein the microorganism belongs to the genus Curvularia.

6. The method according to claim 1, wherein the microorganism belongs to the genus Hormonema.

7. The method according to claim 1, wherein the microorganism belongs to the genus Sydowia.

8. The method according to claim 1, wherein the microorganism belongs to the genus Dothiora.

9. The method according to claim 1, wherein the microorganism is a fungus which forms annellation type spores and which belongs to any one of the genera Dothiora, Hormonema, Sydowia, and Pringsheimia.

10. The method according to claim 1, wherein the ester of (S)-γ-halogenated-β-hydroxybutyric acid represented by the general formula (II) is ethyl (S)-γ-chloro-β-hydroxybutyrate.

11. The method according to claim 9, wherein the microorganism (1) belongs to the genus Dothiora or Hormonema, and (2) possesses an 18S rRNA gene comprising the nucleotide sequences shown in SEQ ID NOs. 32 and 33.

12. The method according to claim 9, wherein the microorganism (1) belongs to the genus Dothiora, and (2) possesses an 18S rRNA gene comprising the nucleotide sequences shown in SEQ ID NOs. 34 and 35.

13. The method according to claim 9, wherein the microorganism (1) belongs to the genus Dothiora, and (2) possesses an 18S rRNA gene comprising the nucleotide sequences shown in SEQ ID NOs. 36 and 37.

14. The method according to claim 8, wherein the microorganism (1) is a fungus which forms no spore, and (2) possesses an 18S rRNA gene comprising the nucleotide sequences shown in SEQ ID NOs. 38 and 39.

15. The method according to claim 9, wherein the microorganism (1) belongs to the genus Hormonema, and (2) possesses an 18S rRNA gene comprising the nucleotide sequences shown in SEQ ID NOs. 40 and 41.

16. The method according to claim 9, wherein the microorganism (1) belongs to the genus Sydowia, and (2) possesses an 18S rRNA gene comprising the nucleotide sequences shown in SEQ ID NOs. 42 and 43.

17. The method according to claim 9, wherein the microorganism (1) belongs to the genus Pringsheimia, and (2) possesses an 18S rRNA gene comprising the nucleotide sequences shown in SEQ ID NOs. 44 and 45.

18. The method according to claim 1, wherein the microorganism (1) is a fungus which forms no spore, (2) belongs to the genus Dothidea, and (3) possesses an 18S rRNA gene comprising the nucleotide sequences shown in SEQ ID NOs. 46 and 47.

19. The method according to claim 1, wherein the microorganism (1) is a fungus which forms no spore, (2) belongs to the genus Selenophoma, and (3) possesses an 18S rRNA gene comprising the nucleotide sequences shown in SEQ ID NOs. 48 and 49.

20. The method according to claim 8, wherein the microorganism (1) is a fungus which forms no spore, and (2) possesses an 18S rRNA gene comprising the nucleotide sequences shown in SEQ ID NOs. 50 and 51.

21. The method according to claim 1, wherein the microorganism (1) is a fungus which forms no spore, (2) belongs to the genus Pringsheimia, and (3) possesses an 18S rRNA gene comprising the nucleotide sequences shown in SEQ ID NOs. 52 and 53.

22. The method according to claim 1, wherein the microorganism (1) is a fungus which forms no spore, (2) belongs to the genus Dothidea, and (3) possesses an 18S rRNA gene comprising the nucleotide sequences shown in SEQ ID NOs. 54 and 55.

23. The method according to claim 1, wherein the microorganism possesses an 18S rRNA gene comprising a first and second nucleotide sequence at positions corresponding to positions 1480–1498 and 1579–1591, respectively, of the *Candida albicans* 18S rRNA gene set forth in SEQ ID NO: 1.

* * * * *

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
( A ) LENGTH: 1788 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Candida albicans
( B ) STRAIN: MUCL29800

( x i ) SEQUENCE DESCRIPTION: SEQ ID NO:1:

```
TATCTGGTTG ATCCTGCCAG TAGTCATATG CTTGTCTCAA AGATTAAGCC ATGCATGTCT   60
AAGTATAAGC AATTTATACA GTGAAACTGC GAATGGCTCA TTAAATCAGT TATCGTTTAT  120
TTGATAGTAC CTTACTACTT GGATAACCGT GGTAATTCTA GAGCTAATAC ATGCTTAAAA  180
TCCCGACTGT TTGGAAGGGA TGTATTTATT AGATAAAAAA TCAATGCCTT CGGGCTCTTT  240
GATGATTCAT AATAACTTTT CGAATCGCAT GGCCTTGTGC TGGCGATGGT TCATTCAAAT  300
TTCTGCCCTA TCAACTTTCG ATGGTAGGAT AGTGGCCTAC CATGGTTTCA ACGGGTAACG  360
GGGAATAAGG GTTCGATTCC GGAGAGGGAG CCTGAGAAAC GGCTACCACA TCCAAGGAAG  420
GCAGCAGGCG CGCAAATTAC CCAATCCCGA TTCAGGGGAG GTAGTGACAA TAAATAACGA  480
TACAGGGCCC TTTTGGGTCT TGTAATTGGA ATGAGTACAA TGTAAATACC TTAACGAGGA  540
ACAATTGGAG GGCAAGTCTG GTGCCAGCAG CCGCGGTAAT TCCAGCTCCA AAAGCGTATA  600
TTAAAGTTGT TGCAGTTAAA AAGCTCGTAG TTGAACTTTG GGCTTGGCTG GCCGGTCCAT  660
CTTTTTCGAT GCGTACTGGA CCAGCCGAGC CTTTCCTTCT GGTAGCCATT TATGGCGAAC  720
CAGGACTTTT ACTTTGAAAA AATTAGAGTG TTCAAAGCAG GCCTTTGCTC GAATATATTA  780
GCATGGAATA ATAGAATAGG ACGTTATGGT TCTATTGTGT TGGTTTCTAG GACCATCGTA  840
```

-continued

| | | | | | | |
|---|---|---|---|---|---|---|
| ATGATTAATA | GGGACGGTCG | GGGGTATCAG | TATTCAGATG | TCGAAAGGTG | AAATTCTTGG | 900 |
| ATTTACTGAA | GACTAACTAC | TGCGAAAGCA | TTTACCAAGG | ACGTTTTCAT | TAATCAAGAA | 960 |
| CGAAAGTTAG | GGGATCGAAG | ATGATCAGAT | ACCGTCGTAG | TCTTAACCAT | AAACTATGCC | 1020 |
| GACTAGGGAT | CGGTTGTTGT | TCTTTTATTG | ACGCAATCGG | CACCTTACGA | GAAATCAAAG | 1080 |
| TCTTTGGGTT | CTGGGGGGAG | TATGGTCGCA | AGGCTGAAAC | TTAAAGGAAT | TGACGGAAGG | 1140 |
| GCACCACCAG | GAGTGGAGCC | TGCGGCTTAA | TTTGACTCAA | CACGGGGAAA | CTCACCAGGT | 1200 |
| CCAGACACAA | TAAGGATTGA | CAGATTGAGA | GCTCTTTCTT | GATTTTGTGG | GTGGTGGTGC | 1260 |
| ATGGCCGTTC | TTAGTTGGTG | GAGTGATTTG | TCTGCTTAAT | TGCGATAACG | AACGAGACCT | 1320 |
| TAACCTACTA | AATAGTGCTG | CTAGCATTTG | CTGGTATAGT | CACTTCTTAG | AGGGACTATC | 1380 |
| GACTCCAAGT | CGATGGAAGT | TTGAGGCAAT | AACAGGTCTG | TGATGCCCTT | AGACGTTCTG | 1440 |
| GGCCGCACGC | GCGCTACACT | GACGGAGCCA | GCGAGTATAA | GCCTTGGCCG | AGAGGTCTGG | 1500 |
| GAAATCTTGT | GAAACTCCGT | CGTGCTGGGG | ATAGAGCATT | GTAATTGTTG | CTCTTCAACG | 1560 |
| AGGAATTCCT | AGTAAGCGCA | AGTCATCAGC | TTGCGTTGAT | TACGTCCCTG | CCCTTTGTAC | 1620 |
| ACACCGCCCG | TCGCTACTAC | CGATTGAATG | GCTTAGTGAG | GCCTCCGGAT | TGGTTTAGGA | 1680 |
| AAGGGGGCAA | CTCCATTCTG | GAACCGAGAA | GCTGGTCAAA | CTTGGTCATT | TAGAGGAAGT | 1740 |
| AAAAGTCGTA | ACAAGGTTTC | CGTAGGTGAA | CCTGCGGAAG | GATCATTA | | 1788 |

( 2 ) INFORMATION FOR SEQ ID NO:2:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Aureobasidium pullulans var. pullulans
( B ) STRAIN: ATCC34621

( x i ) SEQUENCE DESCRIPTION: SEQ ID NO:2:

| | | | | | | |
|---|---|---|---|---|---|---|
| AAACTTAAAG | GAATTGACGG | AAGGGCACCA | CCAGGAGTGG | AGCCTGCGGC | TTAATTTGAC | 60 |
| TCAACACGGG | GAAACTCACC | AGGTCCAGAC | ACAATAAGGA | TTGACAGATT | GAGAGCTCTT | 120 |
| TCTTGATTTC | GTGGGTGGTG | GTGCATGGCC | GTTCTTAGTT | GGTGGAGTGA | TTTGTCTGCT | 180 |
| TAATTGCGAT | AACGAACGAG | ACCTTAACCT | GCTAAATAGC | CCGGCCCGCT | TTGGCGGGTC | 240 |
| GCCGGCTTCT | TAGAGGGACT | ATCGGCTCAA | GCCGATGGAA | GTTTGAGGCA | ATAACAGGTC | 300 |
| TGTGATGCCC | TTAGATGTTC | TGGGCCGCAC | GCGCGCTACA | CTGACAGAGC | CAACGAGTTC | 360 |
| ATTTCCTTGC | CCGGAAGGGT | TGGGTAATCT | CGTTAAACTC | TGTCGTGCTG | GGGATAGAGC | 420 |
| ATTGCAATTA | TTGCTCTTCA | ACGAGGAATG | CCTAGTAAGC | GTACGTCATC | AGCGTGCGTT | 480 |
| GATTACGTCC | CTGCCCTTTG | TACACACCGC | CCGT | | | 514 |

( 2 ) INFORMATION FOR SEQ ID NO:3:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:

-continued (A) ORGANISM: Aureobasidium pullulans var. pullulans
(B) STRAIN: CBS123.37

(xi) SEQUENCE DESCRIPTION: SEQ ID NO:3:

```
AAACTTAAAG GAATTGACGG AAGGGCACCA CCAGGCGTGG AGCCTGCGGC TTAATTTGAC    60
TCAACACGGG GAAACTCACC AGGTCCAGAC ACAATAAGGA TTGACAGATT GAGAGCTCTT   120
TCTTGATTTT GTGGGTGGTG GTGCATGGCC GTTCTTAGTT GGTGGAGTGA TTTATCTGCT   180
TAATTGCGAT AACGAACGAG ACCTTAACCT GCTAAATAGC CCGGCCCGCT TTGGCGGGTC   240
GCCGGCTTCT TAGAGGGACT ATCGGCTCAA GCCGATGGAA GTTTGAGGCA ATAACAGGTC   300
TGTGATGCCC TTAGATGTTC TGGGCCGCAC GCGCGCTACA CTGACAGAGC CAACGAGTTC   360
ATTTCCTTGC CCGGAAGGGT TGGGTAATCT TGTTAAACTC TGTCGTGCTG GGGATAGAGC   420
ATTGCAATTA TTGCTCTTCA ACGAGGAATG CCTAGTAAGC GTACGTCATC AGCGTGCGTT   480
GATTACGTCC CTGCCCTTTG TACACACCGC CCGT                               514
```

(2) INFORMATION FOR SEQ ID NO:4:

(i) SEQUENCE CHARACTERISTICS:
(A) LENGTH: 514 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Aureobasidium pullulans var. pullulans
(B) STRAIN: CBS146.30

(xi) SEQUENCE DESCRIPTION: SEQ ID NO:4:

```
AAACTTAAAG GAATTGACGG AAGGGCACCA CCAGGCGTGG AGCCTGCGGC TTAATTTGAC    60
TCAACACGGG GAAACTCACC AGGTCCAGAC ACAATAAGGA TTGACAGATT GAGAGCTCTT   120
TCTTGATTTT GTGGGTGGTG GTGCATGGCC GTTCTTAGTT GGTGGAGTGA TTTGTCTGCT   180
TAATTGCGAT AACGAACGAG ACCTTAACCT GCTAAATAGC CCGGCCCGCT TTGGCGGGTC   240
GCCGGCTTCT TAGAGGGACT ATCGGCTCAA GCCGATGGAA GTTTGAGGCA ATAACAGGTC   300
TGTGATGCCC TTAGATGTTC TGGGCCGCAC GCGCGCTACA CTGACAGAGC CAACGAGTTC   360
ATTTCCTTGC CCGGAAGGGT TGGGTAATCT TGTTAAACTC TGTCGTGCTG GGGATAGAGC   420
ATTGCAATTA TTGCTCTTCA ACGAGGAATG CCTAGTAAGC GTACGTCATC AGCGTGCGTT   480
GATTACGTCC CTGCCCTTTG TACACACCGC CCGT                               514
```

(2) INFORMATION FOR SEQ ID NO:5:

(i) SEQUENCE CHARACTERISTICS:
(A) LENGTH: 515 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Aureobasidium pullulans var. pullulans
(B) STRAIN: CBS701.76

(xi) SEQUENCE DESCRIPTION: SEQ ID NO:5:

```
AAACTTAAAG GAATTGACGG AAGGGCACCA CCAGGCGTGG TGCCTGCGGC TTAATTTGAC    60
TCAACACGGG GAAACTCACC AGGTCCAGAC ACATTAAGGA TTGACAGATT GAGAGCTCTT   120
TCTTGATTTC GTGGGTGGTG GTGCATGGCC GCTCTTAGTT GGTGGAGTGA TTTGTCTGCT   180
```

TAATTGCGAT AACGAACGAG ACCTTAACCT GCTAAATAGC CCGGCCCGCT TTGGCGGGTC 240

GTCGGCTTCT TAGAGGGACT ATCGGCTCAA GCGCGATGGA AGTTTGAGGC AATAACAGGT 300

CTGTGATGCC CTTAGATGTT CTGGGCCGCA CGCGCGCTAC ACTGACAGAG CCAACGAGTT 360

CATTTCCTTG CCCGGAAGGG TTGGGTAATC TTGTTAAACT CTGTCGTGCT GGGGATAGAG 420

CATTGCAATT ATTGCTCTTC AACGAGGAAT GCCTAGTAAG CGTACGTCAT CAGCGTGCGT 480

TGATTACGTC CCTGCCCTTT GTACACACCG CCCGT 515

( 2 ) INFORMATION FOR SEQ ID NO:6:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Aureobasidium pullulans var. pullulans
( B ) STRAIN: MCI3251

( x i ) SEQUENCE DESCRIPTION: SEQ ID NO:6:

AAACTTAAAG GAATTGACGG AAGGGCACCA CCAGGCGTGG AGCCTGCGGC TTAATTTGAC 60

TCAACACGGG GAAACTCACC AGGTCCAGAC ACAATAAGGA TTGACAGATT GAGAGCTCTT 120

TCTTGATTTT GTGGGTGGTG GTGCATGGCC GTTCTTAGTT GGTGGAGTGA TTTGTCTGCT 180

TAATTGCGAT AACGAACGAG ACCTTAACCT GCTAAATAGC CCGGCCCGCT TTGGCGGGTC 240

GCCGGCTTCT TAGAGGGACT ATCGGCTCAA GCCGATGGAA GTTTGAGGCA ATAACAGGTC 300

TGTGATGCCC TTAGATGTTC TGGGCCGCAC GCGCGCTACA CTGACAGAGC CAACGAGTTC 360

ATTTCCTTGC CCGGAAGGGT TGGGTAATCT TGTTAAACTC TGTCGTGCTG GGGATAGAGC 420

ATTGCAATTA TTGCTCTTCA ACGAGGAATG CCTAGTAAGC GTACGTCATC AGCGTGCGTT 480

GATTACGTCC CTGCCCTTTG TACACACCGC CCGT 514

( 2 ) INFORMATION FOR SEQ ID NO:7:

( i ) SEQUENCE CHARACTERISTICS:
( A ) LENGTH: 513 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Aureobasidium pullulans var. pullulans
( B ) STRAIN: MCI3252

( x i ) SEQUENCE DESCRIPTION: SEQ ID NO:7:

AAACTTAAAG GAATTGACGG AAGGCACCAA CCAGGCGTGG AGCTGCGGCT TAATTTGACT 60

CAACACGGGG AAACTCACCA GGTCCAGACA CAATAAGGAT TGACAGATTG AGAGCTCTTT 120

CTTGATTTTG TGGGTGGTGG TGCATGGCCG TTCTTAGTTG GTGGAGTGAT TTGTCTGCTT 180

AATTGCGATA ACGAACGAGA CCTTAACCTG CTAAATAGCC CGGCCCGCTT TGGCGGGTCG 240

CCGGCTTCTT AGAGGGACTA TCGGCTCAAG CCGATGGAAG TTTGAGGCAA TAACAGGTCT 300

GTGATGCCCT TAGATGTTCT GGGCCGCACG CGCGCTACAC TGACAGAGCC AACGAGTTCA 360

TTTCCTTGCC CGGAAGGGTT GGGTAATCTT GTTAAACTCT GTCGTGCTGG GGATAGAGCA 420

TTGCAATTAT TGCTCTTCAA CGAGGAATGC CTAGTAAGCG TACGTCATCA GCGTGCGTTG 480

ATTACGTCCC TGCCCTTTGT ACACACCGCC CGT 513

( 2 ) INFORMATION FOR SEQ ID NO:8:

( i ) SEQUENCE CHARACTERISTICS:
( A ) LENGTH: 512 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Aureobasidium microsticutum
( B ) STRAIN: IFO32070

( x i ) SEQUENCE DESCRIPTION: SEQ ID NO:8:

AAACTTAAAG AAATTGACGG AAGGGCACAC CAGGCGTGGA CCTGCGGCTT AATTTGACTC 60
AACACGGGGA AACTCACCAG GTCCAGACAC AATAAGGGAT TGACAGATTG AGAGCTCTTT 120
CTTGATTTTG TGGGTGGTGG TGCATGGCCG TTCTTAGTTG GTGGAGTGAT TTGTCTGCTT 180
AATTGCGATA ACGAACGAGA CCTAACCTGC TAAATAGCCC GGCCCGCTTT GGCGGGTCGC 240
CGGCTTCTTA GAGGGACTAT CGGCTCAAGC CGATGGAAGT TTGAGGCAAT AACAGGTCTG 300
TGATGCCCTT AGATGTTCTG GGCCGCACGC GCGCTACACT GACAGAGCCA ACGAGTTCAT 360
TTCCTTGCCC GGAAGGGTTG GGTAATCTTG TTAAACTCTG TCGTGCTGGG GATAGAGCAT 420
TGCAATTATT GCTCTTCAAC GAAGAATGCC TAGTAAGCGT ACGTCATCAG CGTGCGTTGA 480
TTACGTCCCT GCCCTTTGTA CACACCGCCC GT 512

( 2 ) INFORMATION FOR SEQ ID NO:9:

( i ) SEQUENCE CHARACTERISTICS:
( A ) LENGTH: 515 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora cannavinae
( B ) STRAIN: CBS737.71

( x i ) SEQUENCE DESCRIPTION: SEQ ID NO:9:

AAACTTAAAG GAATTGACGG AAGGGCACCA CCAGGCGTGG AGCCTGCGGC TTAATTTGAC 60
TCAACACGGG GAAACTCACC AGGTCCAGAC ACAATAAGGA TTGACAGATT GAGAGCTCTT 120
TCTTGATTTT GTGGGTGGTG GTGCATGGCC GTTCTTAGTT GGTGGAGTGA TTTGTCTGCT 180
TAATTGCGAT AACGAACGAG ACCTTAACCT GCTAAATAGC CCGGCCCGCT TTGGCGGGTC 240
GCCGGCTTCT TAGAGGGACT ATCGGCTCAA GCCGATGGAA GTTTGAGGCA ATAACAGGTC 300
TGTGATGCCC TTAGATGTTC TGGGCCGCAC GCGCGCTACA CTGACAGAGC CAACGAGTTC 360
ATCACCTTGG CCGGAAGGTC TGGGTAATCT TGTTAAACTC TGTCGTGCTG GGGATAGAGC 420
ATTGCAATTA TTGCTCTTCA ACGAGGAATG CCTAGTAAGC GCATGTCATC AGCATGCGTT 480
GATTACGTGC CCTGCCCTTT GTACACACCG CCCGT 515

( 2 ) INFORMATION FOR SEQ ID NO:10:

( i ) SEQUENCE CHARACTERISTICS:
( A ) LENGTH: 514 base pairs
( B ) TYPE: nucleic acid
( C ) STRANDEDNESS: double ( D ) TOPOLOGY: linear ( i i ) MOLECULE TYPE: Genomic DNA ( v i ) ORIGINAL SOURCE:
( A ) ORGANISM: Dothiora elliptica
( B ) STRAIN: CBS736.71

( x i ) SEQUENCE DESCRIPTION: SEQ ID NO:10:

AAACTTAAAG GAATTGACGG AAGGGCACCA CCAGGCGTGG AGCCTGCGGC TTAATTTGAC 60
TCAACACGGG GAAACTCACC AGGTCCAGAC ACAATAAGGA TTGACAGATT GAGAGCTCTT 120
TCTTGATTTT GTGGGTGGTG GTGCATGGCC GTTCTTAGTT GGTGGAGTGA TTTGTCTGCT 180
TAATTGCGAT AACGAACGAG ACCTTAACCT GCTAAATAGC CCGGCCCGCT TTGGCGGGTC 240
GCCGGCTTCT TAGAGGGACT ATCGGCTCAA GCCGATGGAA GTTTGAGGCA ATAACAGGTC 300
TGTGATGCCC TTAGATGTTC TGGGCCGCAC GCGCGCTACA CTGACAGAGC CAACGAGTTC 360
ATCACCTTGG CCGGAAGGTC TGGGTAATCT TGTTAAACTC TGTCGTGCTG GGGATAGAGC 420
ATTGCAATTA TTGCTCTTCA ACGAGGAATG CCTAGTAAGC GCATGTCATC AGCATGCGTT 480
GATTACGTCC CTGCCCTTTG TACACACCGC CCGT 514

( 2 ) INFORMATION FOR SEQ ID NO:11:

( i ) SEQUENCE CHARACTERISTICS:
( A ) LENGTH: 513 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora phaeosperma
( B ) STRAIN: CBS870.71

( x i ) SEQUENCE DESCRIPTION: SEQ ID NO:11:

AAACTTAAAG AAATTGACGG AAGGGCACCA CCAGGCGTGG AGCCTGCGGC TTAATTTGAC 60
TCAACACGGG GAAACTCACC AGGTCCAGAC ACAATAAGGA TTGACAGATT GAGAGCTCTT 120
TCTTGATTTT GTGGGTGGTG GTGCATGGCC GTTCTTAGTT GGTGGAGTGA TTTGTCTGCT 180
TAATTGCGAT AACGAAGGAG ACTTAACCTG CTAAATAGCC CGGCCCGCTT TGGCGGGTCG 240
CCGGCTTCTT AGAGGGACTA TCGGCTCAAG CCGATGGAAG TTTGAGGCAA TAACAGGTCT 300
GTGATGCCCT TAGATGTTCT GGGCCGCACG CGCGCTACAC TGACAGAGCC AACGAGTTCA 360
TCACCTTGGC CGGAAGGTCT GGGTAATCTT GTTAAACTCT GTCGTGCTGG GGATAGAGCA 420
TTGCAATTAT TGCTCTTCAA CGAGGAATGC CTAGTAAGCG CATGTCATCA GCATGCGTTG 480
ATTACGTCCC TGCCCTTTGT ACACACCGCC CGT 513

( 2 ) INFORMATION FOR SEQ ID NO:12:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora rhamni- alpinae
( B ) STRAIN: CBS745.71

( x i ) SEQUENCE DESCRIPTION: SEQ ID NO:12:

-continued

```
AAACTTAAAG AAATTGACGG AAGGGCACCA CCAGGCGTGG AGCCTGCGGC TTAATTTGAC     60
TCAACACGGG GAAACTCACC AGGTCCAGAC ACAATAAGGA TTGACAGATT GAGAGCTCTT    120
TCTTGATTTT GTGGGTGGTG GTGCATGGCC GTTCTTAGTT GGTGGAGTGA TTTGTCTGCT    180
TAATTGCGAT AACGAACGAG ACCTTAACCT GCTAAATAGC CCGGCCCGCT TTGGCGGGTC    240
GCCGGCTTCT TAGAGGGACT ATCGGCTCAA GCCGATGGAA GTTTGAGGCA ATAACAGGTC    300
TGTGATGCCC TTAGATGTTC TGGGCCGCAC GCGCGCTACA CTGACAGAGC CAACGAGTTC    360
ATCACCTTGG CCGGAAGGTC TGGGTAATCT TGTTAAACTC TGTCGTGCTG GGGATAGAGC    420
ATTGCAATTA TTGCTCTTCA ACGAGGAATG CCTAGTAAGC GCATGTCATC AGCATGCGTT    480
GATTACGTCC CTGCCCTTTG TACACACCGC CCGT                                514
```

( 2 ) INFORMATION FOR SEQ ID NO:13:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Hormonema sp.
( B ) STRAIN: MCI3287

( x i ) SEQUENCE DESCRIPTION: SEQ ID NO:13:

```
AAACTTAAAG AAATTGACGG AAGGGCACCA CACAGGCGTG GAGCTGCGGC TTAATTTGAC     60
TCAACACGGG GAAACTCACC AGGTCCAGAC ACAATAAGGA TTGACAGATT GAGAGCTCTT    120
TCTTGATTTT GTGGGTGGTG GTGCATGGCC GTTCTTAGTT GGTGGAGTGA TTTGTCTGCT    180
TAATTGCGAT AACGAACGAG ACCTTAACCT GCTAAATAGC CCGGCCCGCT TTGGCGGGTC    240
GCCGGCTTCT TAGAGGGACT ATCGGCTCAA GCCGATGGAA GTTTGAGGCA ATAACAGGTC    300
TGTGATGCCC TTAGATGTTC TGGGCCGCAC GCGCGCTACA CTGACAGAGC CAACGAGTTC    360
ATCACCTTGG CCGGAAGGTC TGGGTAATCT TGTTAAACTC TGTCGTGCTG GGGATAGAGC    420
ATTGCAATTA TTGCTCTTCA ACGAGGAATG CCTAGTAAGC GCATGTCATC AGCATGCGTT    480
GATTACGTCC CTGCCCTTTG TACACACCGC CCGT                                514
```

( 2 ) INFORMATION FOR SEQ ID NO:14:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Hormonema sp.
( B ) STRAIN: MCI3468

( x i ) SEQUENCE DESCRIPTION: SEQ ID NO:14:

```
AAACTTAAAG AAATTGACGG AAGGGCACCA CCAGGCGTGG AGCCTGCGGC TTAATTTGAC     60
TCAACACGGG GAAACTCACC AGGTCCAGAC ACAATAAGGA TTGACAGATT GAGAGCTCTT    120
TCTTGATTTT GTGGGTGGTG GTGCATGGCC GTTCTTAGTT GGTGGAGTGA TTTGTCTGCT    180
TAATTGCGAT AACGAACGAG ACCTTAACCT GCTAAATAGC CCGGCCCGCT TTGGCGGGTC    240
GCCGGCTTCT TAGAGGGACT ATCGGCTCAA GCCGATGGAA GTTTGAGGCA ATAACAGGTC    300
```

-continued

TGTGATGCCC TTAGATGTTC TGGGCCGCAC GCGCGCTACA CTGACAGAGC CAACGAGTTC 360

ATCACCTTGG CCGGAAGGTC TGGGTAATCT TGTTAAACTC TGTCGTGCTG GGGATAGAGC 420

ATTGCAATTA TTGCTCTTCA ACGAGGAATG CCTAGTAAGC GCATGTCATC AGCATGCGTT 480

GATTACGTCC CTGCCCTTTG TACACACCGC CCGT 514

( 2 ) INFORMATION FOR SEQ ID NO:15:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora europaea
( B ) STRAIN: CBS738.71

( x i ) SEQUENCE DESCRIPTION: SEQ ID NO:15:

AAACTTAAAG GAATTGACGG AAGGGTACCA CCAGGCGTGG AGCCTGAGGC TTAATTTGAC 60

TCAACACGGG GAAACTCACC AGGTCCAGAC ACAATACGGA TTGACAGATT GAGAGCTCTC 120

TCTTGATTTT GTGGCTGGCG GTGCATGGCC GTTCTTAGTT GGCGGAGTGA TTTGTCTGCT 180

TAATTGCGAT AACGAACGAG ACCTTAACCT GCTAAATAGC CCGGCCCGCT TTGGCGGGTC 240

GCCGGCTTCT TAGAGGGACT ATCGGCTCAA GCCGATGGAA GTTTGAGGCA ATAACAGGTC 300

TGTGATGCCC TTAGATGTTC TGGGCCGCAC GCGCGCTACA CTGACAGAGC CAACGAGATC 360

ATCACCTTGC CGGAAGGTCT GGGTAATCTT GTTAAACTCT GTCGTGCTGG GGATAGAGCA 420

TTGCAATTAT TGCTCTTCAA CGAGGAATGC CTAGTAAGCG CATGTCATCA GCATGCGTTG 480

ATTACGTGCC CTGCCCTTTG TACACACCGC CCGT 514

( 2 ) INFORMATION FOR SEQ ID NO:16:

( i ) SEQUENCE CHARACTERISTICS:
( A ) LENGTH: 513 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora laureolae
( B ) STRAIN: CBS744.71

( x i ) SEQUENCE DESCRIPTION: SEQ ID NO:16:

AAACTTAAAG AAATTGACGG AAGGGCACCA CCAGGCGTGG AGCCTGCGGC TTAATTTGAC 60

TCAACACGGG GAAACTCACC AGGTCCAGAC ACAATAAGGA TTGACAGATT GAGAGCTCTT 120

TCTTGATTTT GTGGGTGGTG GTGCATGGCC GTTCTTAGTT GGTGGAGTGA TTTGTCTGCT 180

TAATTGCGAT AACGAACGAG ACCTTAACCT GCTAAATAGC CCGGCCCGCT TTGGCGGGTC 240

GCCGGCTTCT TAGAGGGACT ATCGGCTCAA GCCGATGGAA GTTTGAGGCA ATAACAGGTC 300

TGTGATGCCC TTAGATGTTC TGGGCCGCAC GCGCGCTACA CTGACAGAGC CAACGAGTTC 360

ATCACCTTGG CCGGAAGTCT GGGTAATCTT GTTAAACTCT GTCGTGCTGG GGATAGAGCA 420

TTGCAATTAT TGCTCTTCAA CGAGGAATGC CTAGTAAGCG CATGTCATCA GCATGCGTTG 480

ATTACGTCCC TGCCCTTTGT ACACACCGCC CGT 513

( 2 ) INFORMATION FOR SEQ ID NO:17:

-continued ( i ) SEQUENCE CHARACTERISTICS:
( A ) LENGTH: 513 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora schizospora
( B ) STRAIN: CBS189.55

( x i ) SEQUENCE DESCRIPTION: SEQ ID NO:17:

AAACTTAAAG AAATTGACGG AAGGGCACCA CCAGGCGTGG AGCCTGCGGC TTAATTTGAC 60

TCAACACGGG GAAACTCACC AGGTCCAGAC ACAATAAGGA TTGACAGATT GAGAGCTCTT 120

TCTTGATTTT GTGGGTGGTG GTGCATGGCC GTTCTTAATT GGTGGAGTGA TTTGTCTGCT 180

TAATTGCGAT AACGAACGAA ACCTTAACCT GCTAAATAGC CCGGCCCGCT TTGGCGGGTC 240

GCCGGCTTCT TAGAGGGACT ATCGGCTCAA GCCGATGGAA GTTTGAGGCA ATAACAGGTC 300

TGTGATGCCC TTAGATGTTC TGGGCCGCAC GCGCGCTACA CTGACAGAGC CAACGAGTTC 360

ATCACCTTGG CCGGAAGTCT GGGTAATCTT GTTAAACTCT GTCGTGCTGG GGATAGAGCA 420

TTGCAATTAT TGCTCTTCAA CGAAGAATGC CTAGTAAGCG CATGTCATCA GCATGCGTTG 480

ATTACGTCCC TGCCCTTTGT ACACACCGCC CGT 513

( 2 ) INFORMATION FOR SEQ ID NO:18:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Hormonema prunorum
( B ) STRAIN: CBS933.72

( x i ) SEQUENCE DESCRIPTION: SEQ ID NO:18:

AAACTTAAAG GAATTGACGG AAGGGCACCA CCAGGCGTGG AGCCTGCGGC TTAATTTGAC 60

TCAACACGGG GAAACTCACC AGGTCCAGAC ACAATAAGGA TTGACAGATT GAGAGCTCTT 120

TCTTGATTTC ATGGGTGGTG GTGCATGCCC GTTCTTAGTT GGTGGAGTGA TTTGTCTGCT 180

TAATTGCGAT AACGAACGAG ACCTTAACCT GCTAAATAGC CCGGCCCGCT TTGGCGGGTC 240

GCCGGCTTCT TAGAGGGACT ATCGGCTCAA GCCGATGGAA GTTTGAGGCA ATAACAGGTC 300

TGTGATGCCC TTAGATGTTC TGGGCCGCAC GCGCGCTACA CTGACAGAGC CAACGAGTTC 360

ATCACCTTGA CCGGAAGGTC TGGGTAATCT TGTTAAACTC TGTCGTGCTG GGGATAGAGC 420

ATTGCAATTA TTGCTCTTCA ACGAGGAATG CCTAGTAAGC GCATGTCATC AACATGCGTT 480

GATTACGTCC CTGCCCTTTG TACACACCGC CCGT 514

( 2 ) INFORMATION FOR SEQ ID NO:19:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:

(A) ORGANISM: Sydowia polyspora
(B) STRAIN: CBS116.29

(xi) SEQUENCE DESCRIPTION: SEQ ID NO:19:

AAACTTAAAG GAATAGACGG AAGGGCACCA CCAGGCGTGG AGCCTGCGGC TTAATTTGAC 60

TCAACACGGG GAAACTCACC AGGTCCAGAC ACAATAAGGA TTGACAGATT GAGAGCTCTT 120

TCTTGATTTC GTGGGTGGTG GTGCATGGCC GCTCTTAGTT GGTGGAGTGA TTTGTCTGCT 180

TAATTGCGAT AACGAACGAG ACCTTAACCT GCTAAATAGC CCGGTCCGCT TTGGCGGGCC 240

GCCGGCTTCT TAGAGGGACT ATCGGCTCAA GCCGATGGAA GTTTGAGGCA ATAACAGGTC 300

TGTGATGCCC TTAGATGTTC TGGGCCGCAC GCGCGCTACA CTGACAGAGC CAACGAGTTC 360

ATCACCTTGT CCGGAAGGAT TGGGTAATCT TGTTAAACTC TGTCGTGCTG GGGATAGAGC 420

ATTGCAATTA TTGCTCTTCA ACGAGGAATG CCTAGTAAGC GCATGTCATC AGCATGCGTT 480

GATTACGTCC CTGCCCTTTG TACACACCGC CCGT 514

(2) INFORMATION FOR SEQ ID NO:20:

(i) SEQUENCE CHARACTERISTICS:
(A) LENGTH: 513 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Pringsheimia sepincola
(B) STRAIN: CBS748.71

(xi) SEQUENCE DESCRIPTION: SEQ ID NO:20:

AAACTTAAAG AAATTGACGG AAGGGCACCA CCAGGCGTGG AGCCTGCGGC TTAATTTGAC 60

TCAACACGGG GAAACTCACC AGGTCCAGAC ACAATAAGGA TTGACAGATT GAGAGCTCTT 120

TCTTGATTTT GTGGGTGGTG GTGCATGGCC GTTCTTAGTT GGTGGAGTGA TTTGTCTGCT 180

TAATTGCGAT AACGAACGAG ACCTTAACCT GCTAAATAGC CCGGCCCGCT TTGGCGGGTC 240

GCCGGCTTCT TAGAGGGACT ATCGGCTCAA GCCGATGGAA GTTTGAGGCA ATAACAGGTC 300

TGTGATGCCC TTAGATGTTC TGGGCCGCAC GCGCGCTACA CTGACAGAGC CAACGAGTTC 360

ATTTCCTTGT CCGAAAGGTC TGGGTAATCT TGTTAAACTC TGTCGTGCTG GGGATAGAGC 420

ATTGCAATTA TTGTCTTCAA CGAGGAATGC CTAGTAAGCG TACGTCATCA GCGTGCGTTG 480

ATTACGTCCC TGCCCTTTGT ACACACCGCC CGT 513

(2) INFORMATION FOR SEQ ID NO:21:

(i) SEQUENCE CHARACTERISTICS:
(A) LENGTH: 514 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Selenophoma mahoniae
(B) STRAIN: CBS388.92

(xi) SEQUENCE DESCRIPTION: SEQ ID NO:21:

AAACTTAAAG AAATTGACGG AAGGGCACCA CCAGGCGTGG AGCCTGCGGC TTAATTTGAC 60

TCAACACGGG GAAACTCACC AGGTCCAGAC ACAATAAGGA TTGACAGATT GAGAGCTCTT 120

TCTTGATTTT GTGGGTGGTG GTGCATGGCC GTTCTTAGTT GGTGGAGTGA TTTGTCTGCT 180

-continued

TAATTGCGAT AACGAACGAG ACCTTAACCT GCTAAATAGC CCGGCCCGCT TTGGCGGGTC 240

GCCGGCTTCT TAGAGGGACT ATCGGCTCAA GCCGATGGAA GTTTGAGGCA ATAACAGGTC 300

TGTGATGCCC TTAGATGTTC TGGGCCGCAC GCGCGCTACA CTGACAGAGC CAACGAGTTC 360

ATTTCCTTGC CCGGAAGGGT TGGGTAATCT TGTTAAACTC TGTCGTGCTG GGGATAGAGC 420

ATTGCAATTA TTGCTCTTCA ACGAGGAATG CCTAGTAAGC GTACGTCATC AGCGTGCGTT 480

GATTACGTCC CTGCCCTTTG TACACACCGC CCGT 514

( 2 ) INFORMATION FOR SEQ ID NO:22:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Discosphaerian fagi
( B ) STRAIN: CBS171.93

( x i ) SEQUENCE DESCRIPTION: SEQ ID NO:22:

AAACTTAAAG AAATTGACGG AAGGGCACCA CCAGGCGTGG AGCCTGCGGC TTAATTTGAC 60

TCAACACGGG GAAACTCACC AGGTCCAGAC ACAATAAGGA TTGACAGATT GAGAGCTCTT 120

TCTTGATTTT GTGGGTGGTG GTGCATGGCC GTTCTTAGTT GGTGGAGTGA TTTGTCTGCT 180

TAATTGCGAT AACGAACGAG ACCTTAACCT GCTAAATAGC CCGGCCCGCT TTGGCGGGTC 240

GCCGGCTTCT TAGAGGGACT ATCGGCTCAA GCCGATGGAA GTTTGAGGCA ATAACAGGTC 300

TGTGATGCCC TTAGATGTTC TGGGCCGCAC GCGCGCTACA CTGACAGAGC CAACGAGTTC 360

ATTTCCTTGC CCGGAAGGGT TGGGTAATCT TGTTAAACTC TGTCGTGCTG GGGATAGAGC 420

ATTGCAATTA TTGCTCTTCA ACGAGGAATG CCTAGTAAGC GTACGTCATC AGCGTGCGTT 480

GATTACGTCC CTGCCCTTTG TACACACCGC CCGT 514

( 2 ) INFORMATION FOR SEQ ID NO:23:

( i ) SEQUENCE CHARACTERISTICS:
( A ) LENGTH: 512 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothidea noxia
( B ) STRAIN: CBS171.34

( x i ) SEQUENCE DESCRIPTION: SEQ ID NO:23:

AAACTTAAAG AAATTGACGG AAGGGCACCA CAAGGGGTGG AGCCTGCGGC TTAATTTGAC 60

TCAACACGGG GAAACTCACC AGGTCCAGAC ACAACTAGGA TTGACAGATT GAGAGCTCTT 120

TCTTGATTTT GTGGGTGGTG GTGCATGGCC GTTCTTAGTT GGTGGAGTGA TTTGTCTGCT 180

TAATTGCGAT AACGAACGAG ACCTTAACCT GCTAAATAGC CCGTTCCGCT TAGGCGGAAC 240

GCTGGCTTCT TAGAGGGACT ATCGGCTCAA GCCGATGGAA GTTTGAGGCA ATAACAGGTC 300

TGTGATGCCC TTAGATGTTC TGGGCCGCAC GCGCGCTACA CTGACAGAGC CAGCGAGTTC 360

CTCCTTGGCT GGAAAGCCCG GGTAATCTTG TGAAACTCTG TCGTGCTGGG GATAGAGCAT 420

TGCAATTATT GCTCTTCAAC GAGGAATCCC TAGTAAGCGC AAGTCATCAG CTTGCGTTGA 480

-continued

TTACGTCCCT GCCCTTTGTA CACACCGCCC GT 512

(2) INFORMATION FOR SEQ ID NO:24:

(i) SEQUENCE CHARACTERISTICS:
(A) LENGTH: 513 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Dothidea muelleri
(B) STRAIN: CBS191.58

(xi) SEQUENCE DESCRIPTION: SEQ ID NO:24:

AAACTTAAAG AAATTGACGG AAGGGCACCA CCAGGCGTGG AGCCTGCGGC TTAATTTGAC 60

TCAACACGGG GAAACTCACC AGGTCCAGAC ACAATAAGGA TTGACAGATT GAGAGCTCTT 120

TCTTGATTTT GTGGGTGGTG GTGCATGGCC GTTCTTACTT GGTGGAGTGA TTTGTCTGCT 180

TAATTGCGAT AACGAACGAG ACTTAACCTG CTAAATAGCC CGGCCCGCTT TGGCGGGTCG 240

CCGGCTTCTT AGAGGGACTA TCGGCTCAAG CCGATGGAAG TTTGAGGCAA TAACAGGTCT 300

GTGATGCCCT TAGATGTTCT GGGCCGCACG CGCGCTACAC TGACAGAGCC AACGAGTTCA 360

TCACCTTGGC CGAAAGGTCT GGGTAATCTT GTTAAACTCT GTCGTGCTGG GGATAGAGCA 420

TTGCAATTAT TGCTCTTCAA CGAGGAATGC CTAGTAAGCG CATGTCATCA GCATGCGTTG 480

ATTACGTCCC TGCCCTTTGT ACACACCGCC CGT 513

(2) INFORMATION FOR SEQ ID NO:25:

(i) SEQUENCE CHARACTERISTICS:
(A) LENGTH: 514 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Dothidea sambuci
(B) STRAIN: CBS197.58

(xi) SEQUENCE DESCRIPTION: SEQ ID NO:25:

AAACTTAAAG AAATTGACGG AAGGGCACCA CCAGGCGTGG AGCCTGCGGC TTAATTTGAC 60

TCAACACGGG GAAACTCACC AGGTCCAGAC ACAATAAGGA TTGACAGATT GAGAGCTCTT 120

TCTTGATTTT GTGGGTGGTG GTGCATGGCC GTTCTTAGTT GGTGGAGTGA TTTGTCTGCT 180

TAATTGCGAT AACGAACGAG ACCTTAACCT GCTAAATAGC CCGGCCCGCT TTGGCGGGTC 240

GCCGGCTTCT TAGAGGGACT ATCGGCTCAA GCCGATGGAA GTTTGAGGCA ATAACAGGTC 300

TGTGATGCCC TTAGATGTTC TGGGCCGCAC GCGCGCTACA CTGACAGAGC CAACGAGTTC 360

ATCACCTTGG CCGAAAGGTC TGGGTAATCT TGTTAAACTC TGTCGTGCTG GGGATAGAGC 420

ATTGCAATTA TTGCTCTTCA ACGAGGAATG CCTAGTAAGC GCATGTCATC AGCATGCGTT 480

GATTACGTCC CTGCCCTTTG TACACACCGC CCGT 514

(2) INFORMATION FOR SEQ ID NO:26:

(i) SEQUENCE CHARACTERISTICS:
(A) LENGTH: 513 base pairs
(B) TYPE: nucleic acid
(C) STRANDEDNESS: double (D) TOPOLOGY: linear (ii) MOLECULE TYPE: Genomic DNA (vi) ORIGINAL SOURCE:
(A) ORGANISM: Selenophoma donacis
(B) STRAIN: CBS417.51

(xi) SEQUENCE DESCRIPTION: SEQ ID NO:26:

```
AAACTTAAAG AAATTGACGG AAGGGCACCA CCAGGGGTGG AGCCTGCGGC TTAATTTGAC    60
TCAACACGGG GAAACTCACC AGGTCCAGAC ACAATGAGGA TTGACAGATT GAGAGCTCTT   120
TCTTGATTTT GTGGGTGGTG GTGCATGGCC GTTCTTAGTT GGTGGAGTGA TTTGTCTGCT   180
TAATTGCGAT AACGAACGAG ACCTTAACCT GCTAAATAGC CCGTATTGCT TTGGCAGTAC   240
GCCGGCTTCT TAGAGGGACT ATCGGCTCAA GCCGATGGAA GTTTGAGGCA ATAACAGGTC   300
TGTGATGCCC TTAGATGTTC TGGGCCGCAC GCGCGTTACA CTGACGGAGC CAGCGAGTAC   360
TCCCTTGGCC GGAAGGCCCG GGTAATCTTG TTAAACTCCG TCGTGCTGGG GATAGAGCAT   420
TGCAATTATT GCTCTTCAAC GAGGAAATCC CTAGTAAGCG CAAGTCATCA GCTTGCGTTG   480
ATTACGTCCC TGCCCTTTGT ACACACCGCC CGT                                513
```

(2) INFORMATION FOR SEQ ID NO:27:

(i) SEQUENCE CHARACTERISTICS:
(A) LENGTH: 514 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Dothiora moravica
(B) STRAIN: CBS266.59

(xi) SEQUENCE DESCRIPTION: SEQ ID NO:27:

```
AAACTTAAAG AAATTGACGG AAGGGCACCA CCAGGCGTGG AGCCTGCGGC TTAATTTGAC    60
TCAACACGGG GAAACTCACC AGGTCCAGAT GAAATAAGGA TTGACAGATT GAGAGCTCTT   120
TCTTGATTTT TCAGGTGGTG GTGCATGGCC GTTCTTAGTT GGTGGAGTGA TTTGTCTGCT   180
TAATTGCGAT AACGAACGAG ACCTTAACCT GCTAAATAGC CAGGCTAGCT TTGGCTGGTC   240
GCCGGCTTCT TAGAGGGACT ATCGGCTCAA GCCGATGGAA GTTTGAGGCA ATAACAGGTC   300
TGTGATGCCC TTAGATGTTC TGGGCCGCAC GCGCGCTACA CTGACAGAGC CAACGAGTTC   360
TTCACCTTGG CCGAAAGGTC TGGGTAATCT TGTTAAACTC TGTCGTGCTG GGGATAGAGC   420
ATTGCAATTA TTGCTCTTCA ACGAGGAATG CCTAGTAAGC GCGTGTCATC AGCATGCGTT   480
GATTACGTCC CTGCCCTTTG TACACACCGC CCGT                               514
```

(2) INFORMATION FOR SEQ ID NO:28:

(i) SEQUENCE CHARACTERISTICS:
(A) LENGTH: 514 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Pringsheimia karelii
(B) STRAIN: CBS374.59

(xi) SEQUENCE DESCRIPTION: SEQ ID NO:28:

-continued

```
AAACTTAAAG AAATTGACGG AAGGGCACCA CCAGGCGTGG AGCCTGCGGC TTAATTTGAC    60
TCAACACGGG GAAACTCACC AGGTCCAGAC ACAATAAGGA TTGACAGATG GAGAGCTCTT   120
TCTTGATTTT GTGGGTGGTG GTGCATGGCC GTTCTTAGTT GGTGGAGTGA TTTGTCTGCT   180
TAATTGCGAT AACGAACGAG ACCTTAACCT GCTAAATAGC CCGGCCCGCT TTGGCGGGTC   240
GCCGGCTTCT TAGAGGGACT ATCGGCTCAA GCCGATGGAA GTTTGAGGCA ATAACAGGTC   300
TGTGATGCCC TTAGATGTTC TGGGCCGCAC GCGCGCTACA CTGACAGAGC CAACGAGTTC   360
ATTTCCTTGG CCGAAAGGTC TGGGTAATCT TGTTAAACTC TGTCGTGCTG GGGATAGAGC   420
ATTGCAATTA TTGCTCTTCA ACGAGGAATG CCTAGTAAGC GTACGTCATC AGCGTGCGTT   480
GATTACGTCC CTGCCCTTTG TACACACCGC CCGT                               514
```

( 2 ) INFORMATION FOR SEQ ID NO:29:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothidea berberidis
( B ) STRAIN: CBS186.58

( x i ) SEQUENCE DESCRIPTION: SEQ ID NO:29:

```
AAACTTAAAG AAATTGACGG AAGGGCACCA CCAGGCGTGG AGCCTGCGGC TTAATTTGAC    60
TCAACACGGG GAAACTCACC AGGTCCAGAC ACAATAAGGA TTGACAGATT GAGAGCTCTT   120
TCTTGATTTT GTGGGTGGTG GTGCATGGCC GTTCTTAGTT GGTGGAGTGA TTTGTCTGCT   180
TAATTGCGAT AACGAACGAG ACCTTAACCT GCTAAATAGC CCGGCCCGCT TTGGCGGGTC   240
GCCGGCTTCT TAGAGGGACT ATCGGCTCAA GCCGATGGAA GTTTGAGGCA ATAACAGGTC   300
TGTGATGCCC TTAGATGTTC TGGGCCGCAC GCGCGCTACA CTGACAGAGC CAACGAGTTC   360
ATCACCTTGG CCGGAAGGTC TGGGTAATCT TGTTAAACTC TGTCGTGCTG GGGATAGAGC   420
ATTGCAATTA TTGCTCTTCA ACGAGGAATG CCTAGTAAGC GCATGTCATC AGCATGCGTT   480
GATTACGTCC CTGCCCTTTG TACACACCGC CCGT                               514
```

( 2 ) INFORMATION FOR SEQ ID NO:30:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Sydowia agharkari
( B ) STRAIN: CBS434.61

( x i ) SEQUENCE DESCRIPTION: SEQ ID NO:30:

```
AAACTTAAAG AAATTGACGG AAGGGCACCA CCAGGCGTGG AGCCTGCGGC TTAATTTGAC    60
TCAACACGGG GAAACTCACC AGGTCCAGAC ACAATAAGGA TTGACAGATT GAGAGCTCTT   120
TCTTGATTTT GTGGGTGGTG GTGCATGGCC GTTCTTAGTT GGTGGAGTGA TTTGTCTGCT   180
TAATTGCGAT AACGAACGAG ACCTTAACCT GCTAAATAGC CCGGCCCGCT TTGGCGGGTC   240
GCCGGCTTCT TAGAAGGACT ATCGGCTCAA GCCGATGGAA GTTTGAGGCA ATAACAGGTC   300
```

-continued

```
TGTGATGCCC TTAGATGTTC TGGGCCGCAC GCGCGCTACA CTGACAGAGC CAACGAGTTC   360
ATTTCCTTGG CCGAAAGGTC TGGGTAATCT TGTTAAACTC TGTCGTGCTG GGGATAGAGC   420
ATTGCAATTA TTGCTCTTCA ACGAAGAATG CCTAGTAAGC GTACGTCATC AGCGTGCGTT   480
GATTACGTCC CTGCCCTTTG TACACACCGC CCGT                                514
```

( 2 ) INFORMATION FOR SEQ ID NO:31:

( i ) SEQUENCE CHARACTERISTICS:
( A ) LENGTH: 514 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Selenophoma linicola
( B ) STRAIN: CBS468.48

( x i ) SEQUENCE DESCRIPTION: SEQ ID NO:31:

```
AAACTTAAAG AAATTGACGG AAGGGCACCA CCAGGCGTGG AGCCTGCGGC TTAATTTGAC    60
TCAACACGGG GAAACTCACC AGGTCCAGAC ACAATAAGGA TTGACAGATT GAGAGCTCTT   120
TCTTGATTTT GTGGGTGGTG GTGCATGGCC GTTCTTAGTT GGTGGAGTGA TTTGTCTGCT   180
TAATTGCGAT AACGAACGAG ACCTTAACCT GCTAAATAGC CCGGCCCGCT TTGGCGGGTC   240
GCCGGCTTCT TAGAGGGACT ATCGGCTCAA GCCGATGGAA GTTTGAGGCA ATAACAGGTC   300
TGTGATGCCC TTAGATGTTC TGGGCCGCAC GCGCGCTACA CTGACAGAGC CAACGAGTTC   360
ATTTCCTTGG CCGGAAGGTC TGGGTAATCT TGTTAAACTC TGTCGTGCTG GGGATAGAGC   420
ATTGCAATTA TTGCTCTTCA ACGAGGAATG CCTAGTAAGC GTACGTCATC AGCGTGCGTT   480
GATTACGTCC CTGCCCTTTG TACACACCGC CCGT                                514
```

( 2 ) INFORMATION FOR SEQ ID NO:32:

( i ) SEQUENCE CHARACTERISTICS:
( A ) LENGTH: 19 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Hormonema sp.
( B ) STRAIN: MCI3287

( x i ) SEQUENCE DESCRIPTION: SEQ ID NO:32:

```
CACCTTGGCC GGAAGGTCT                                                  19
```

( 2 ) INFORMATION FOR SEQ ID NO:33:

( i ) SEQUENCE CHARACTERISTICS:
( A ) LENGTH: 13 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Hormonema sp.
( B ) STRAIN: MCI3287

( x i ) SEQUENCE DESCRIPTION: SEQ ID NO:33:

```
CATGTCATCA GCA                                                        13
```

( 2 ) INFORMATION FOR SEQ ID NO:34:

( i ) SEQUENCE CHARACTERISTICS:
( A ) LENGTH: 18 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora europaea
( B ) STRAIN: CBS738.71

( x i ) SEQUENCE DESCRIPTION: SEQ ID NO:34:

CACCTTGCCG GAAGGTCT 18

( 2 ) INFORMATION FOR SEQ ID NO:35:

( i ) SEQUENCE CHARACTERISTICS:
( A ) LENGTH: 13 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora europaea
( B ) STRAIN: CBS738.71

( x i ) SEQUENCE DESCRIPTION: SEQ ID NO:35:

CATGTCATCA GCA 13

( 2 ) INFORMATION FOR SEQ ID NO:36:

( i ) SEQUENCE CHARACTERISTICS:
( A ) LENGTH: 18 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora laureolae
( B ) STRAIN: CBS744.71

( x i ) SEQUENCE DESCRIPTION: SEQ ID NO:36:

CACCTTGGCC GGAAGTCT 18

( 2 ) INFORMATION FOR SEQ ID NO:37:

( i ) SEQUENCE CHARACTERISTICS:
( A ) LENGTH: 13 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora laureolae
( B ) STRAIN: CBS744.71

( x i ) SEQUENCE DESCRIPTION: SEQ ID NO:37:

CATGTCATCA GCA 13

( 2 ) INFORMATION FOR SEQ ID NO:38:

( i ) SEQUENCE CHARACTERISTICS:
( A ) LENGTH: 18 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora schizospora
( B ) STRAIN: CBS189.55

( x i ) SEQUENCE DESCRIPTION: SEQ ID NO:38:

C A C C T T G G C C G G A A G T C T 1 8

( 2 ) INFORMATION FOR SEQ ID NO:39:

( i ) SEQUENCE CHARACTERISTICS:
( A ) LENGTH: 13 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora schizospora
( B ) STRAIN: CBS189.55

( x i ) SEQUENCE DESCRIPTION: SEQ ID NO:39:

C A T G T C A T C A G C A 1 3

( 2 ) INFORMATION FOR SEQ ID NO:40:

( i ) SEQUENCE CHARACTERISTICS:
( A ) LENGTH: 19 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Hormonema prunorum
( B ) STRAIN: CBS933.72

( x i ) SEQUENCE DESCRIPTION: SEQ ID NO:40:

C A C C T T G A C C G G A A G G T C T 1 9

( 2 ) INFORMATION FOR SEQ ID NO:41:

( i ) SEQUENCE CHARACTERISTICS:
( A ) LENGTH: 13 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Hormonema prunorum
( B ) STRAIN: CBS933.72

( x i ) SEQUENCE DESCRIPTION: SEQ ID NO:41:

C A T G T C A T C A A C A 1 3

( 2 ) INFORMATION FOR SEQ ID NO:42:

( i ) SEQUENCE CHARACTERISTICS:
( A ) LENGTH: 19 base pairs
( B ) TYPE: nucleic acid
( C ) STRANDEDNESS: double (D) TOPOLOGY: linear (ii) MOLECULE TYPE: Genomic DNA (vi) ORIGINAL SOURCE:
(A) ORGANISM: Sydowia polyspora
(B) STRAIN: CBS116.29

(xi) SEQUENCE DESCRIPTION: SEQ ID NO:42:

CACCTTGTCC GGAAGGATT 19

(2) INFORMATION FOR SEQ ID NO:43:

(i) SEQUENCE CHARACTERISTICS:
(A) LENGTH: 13 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Sydowia polyspora
(B) STRAIN: CBS116.29

(xi) SEQUENCE DESCRIPTION: SEQ ID NO:43:

CATGTCATCA GCA 13

(2) INFORMATION FOR SEQ ID NO:44:

(i) SEQUENCE CHARACTERISTICS:
(A) LENGTH: 19 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Pringsheimia sepincola
(B) STRAIN: CBS748.71

(xi) SEQUENCE DESCRIPTION: SEQ ID NO:44:

TTCCTTGTCC GAAAGGTCT 19

(2) INFORMATION FOR SEQ ID NO:45:

(i) SEQUENCE CHARACTERISTICS:
(A) LENGTH: 13 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Pringsheimia sepincola
(B) STRAIN: CBS748.71

(xi) SEQUENCE DESCRIPTION: SEQ ID NO:45:

TACGTCATCA GCG 13

(2) INFORMATION FOR SEQ ID NO:46:

(i) SEQUENCE CHARACTERISTICS:
(A) LENGTH: 19 base pairs
(B) TYPE: nucleic acid
(C) STRANDEDNESS: double
(D) TOPOLOGY: linear (ii) MOLECULE TYPE: Genomic DNA -continued ( v i ) ORIGINAL SOURCE:
( A ) ORGANISM: Dothidea muelleri
( B ) STRAIN: CBS191.58

( x i ) SEQUENCE DESCRIPTION: SEQ ID NO:46:

CACCTTGGCC GAAAGGTCT 19

( 2 ) INFORMATION FOR SEQ ID NO:47:

( i ) SEQUENCE CHARACTERISTICS:
( A ) LENGTH: 13 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothidea muelleri
( B ) STRAIN: CBS191.58

( x i ) SEQUENCE DESCRIPTION: SEQ ID NO:47:

CATGTCATCA GCA 13

( 2 ) INFORMATION FOR SEQ ID NO:48:

( i ) SEQUENCE CHARACTERISTICS:
( A ) LENGTH: 19 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Selenophoma donacis
( B ) STRAIN: CBS417.51

( x i ) SEQUENCE DESCRIPTION: SEQ ID NO:48:

TCCCTTGGCC GGAAGGCCC 19

( 2 ) INFORMATION FOR SEQ ID NO:49:

( i ) SEQUENCE CHARACTERISTICS:
( A ) LENGTH: 13 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Selenophoma donacis
( B ) STRAIN: CBS417.51

( x i ) SEQUENCE DESCRIPTION: SEQ ID NO:49:

CAAGTCATCA GCT 13

( 2 ) INFORMATION FOR SEQ ID NO:50:

( i ) SEQUENCE CHARACTERISTICS:
( A ) LENGTH: 19 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora moravica
( B ) STRAIN: CBS266.59

( x i ) SEQUENCE DESCRIPTION: SEQ ID NO:50:

C A C C T T G G C C   G A A A G G T C T   1 9

( 2 ) INFORMATION FOR SEQ ID NO:51:

( i ) SEQUENCE CHARACTERISTICS:
( A ) LENGTH: 13 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothiora moravica
( B ) STRAIN: CBS266.59

( x i ) SEQUENCE DESCRIPTION: SEQ ID NO:51:

C G T G T C A T C A   G C A   1 3

( 2 ) INFORMATION FOR SEQ ID NO:52:

( i ) SEQUENCE CHARACTERISTICS:
( A ) LENGTH: 19 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Pringsheimia karelii
( B ) STRAIN: CBS374.59

( x i ) SEQUENCE DESCRIPTION: SEQ ID NO:52:

T T C C T T G G C C   G A A A G G T C T   1 9

( 2 ) INFORMATION FOR SEQ ID NO:53:

( i ) SEQUENCE CHARACTERISTICS:
( A ) LENGTH: 13 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Pringsheimia karelii
( B ) STRAIN: CBS374.59

( x i ) SEQUENCE DESCRIPTION: SEQ ID NO:53:

T A C G T C A T C A   G C G   1 3

( 2 ) INFORMATION FOR SEQ ID NO:54:

( i ) SEQUENCE CHARACTERISTICS:
( A ) LENGTH: 19 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothidea berberidis
( B ) STRAIN: CBS186.58

( x i ) SEQUENCE DESCRIPTION: SEQ ID NO:54:

C A C C T T G G C C   G G A A G G T C T   1 9

-continued ( 2 ) INFORMATION FOR SEQ ID NO:55:

( i ) SEQUENCE CHARACTERISTICS:
( A ) LENGTH: 13 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Dothidea berberidis
( B ) STRAIN: CBS186.58

( x i ) SEQUENCE DESCRIPTION: SEQ ID NO:55:

CATGTCATCA GCA 13

( 2 ) INFORMATION FOR SEQ ID NO:56:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( x i ) SEQUENCE DESCRIPTION: SEQ ID NO:56:

CTACTGCGAA AGCATTTGCC AAGG 24

( 2 ) INFORMATION FOR SEQ ID NO:57:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( x i ) SEQUENCE DESCRIPTION: SEQ ID NO:57:

GAGGAAGTAA AAGTCGTAAC AAGG 24